(12) United States Patent
Cheng et al.

(10) Patent No.: US 12,115,151 B2
(45) Date of Patent: Oct. 15, 2024

(54) METHOD OF TREATMENT OF P53 WT TUMORS

(71) Applicant: Dana-Farber Cancer Institute, Inc., Boston, MA (US)

(72) Inventors: Jingwei Cheng, Melrose, MA (US); James Decaprio, Wellesley, MA (US); Donglim Esther Park, Allston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 682 days.

(21) Appl. No.: 17/289,122

(22) PCT Filed: Oct. 28, 2019

(86) PCT No.: PCT/US2019/058319
§ 371 (c)(1),
(2) Date: Apr. 27, 2021

(87) PCT Pub. No.: WO2020/092221
PCT Pub. Date: May 7, 2020

(65) Prior Publication Data
US 2021/0379039 A1    Dec. 9, 2021

Related U.S. Application Data

(60) Provisional application No. 62/752,382, filed on Oct. 30, 2018.

(51) Int. Cl.
*A61K 31/4439*    (2006.01)
*A61K 31/454*    (2006.01)
(Continued)

(52) U.S. Cl.
CPC ........ *A61K 31/4439* (2013.01); *A61K 31/454* (2013.01); *A61K 31/496* (2013.01); *A61K 31/513* (2013.01); *A61P 35/00* (2018.01)

(58) Field of Classification Search
CPC .............. A61K 31/4439; A61K 31/454; A61K 31/496; A61K 31/513; A61P 35/00
(Continued)

(56) References Cited

FOREIGN PATENT DOCUMENTS

WO    WO2018092020 A1 *   3/2018   ......... A61K 31/496

OTHER PUBLICATIONS

Abramson HN. The multiple myeloma drug pipeline—2018: a review of small molecules and their therapeutic targets. Clinical Lymphoma Myeloma and Leukemia. Sep. 1, 2018;18(9):611-27. (Year: 2018).*

(Continued)

*Primary Examiner* — Jeffrey S Lundgren
*Assistant Examiner* — Heather Dahlin
(74) *Attorney, Agent, or Firm* — Foley Hoag LLP

(57) ABSTRACT

The present invention relates to methods of treating p53 wild type (WT) tumors. In particular, the invention provides novel therapies for p53 WT tumors based on the combination of Mouse Double Minute 2 (MDM2) inhibitors, e.g. HDM201, together with Casein Kinase 1 alpha (CK1α) degrading agents and/or an MDM4 inhibitors, e.g. lenalidomide. The combination may be used in the treatment of solid as well as hematologic p53 WT tumors, e.g. Merkel cell carcinoma (MCC) or myelodysplastic syndrome (MDS).

23 Claims, 34 Drawing Sheets

(51) Int. Cl.
  *A61K 31/496* (2006.01)
  *A61K 31/513* (2006.01)
  *A61P 35/00* (2006.01)
(58) Field of Classification Search
  USPC .......................................................... 514/338
  See application file for complete search history.

(56) References Cited

OTHER PUBLICATIONS

Gu D, Wang S, Kuiatse I, Wang H, He J, Dai Y, Jones RJ, Bjorklund CC, Yang J, Grant S, Orlowski RZ. Inhibition of the MDM2 E3 Ligase induces apoptosis and autophagy in wild-type and mutant p53 models of multiple myeloma, and acts synergistically with ABT-737. PLoS One. Sep. 2, 2014;9(9):e103015. (Year: 2014).*

Tornesello ML, Annunziata C, Tornesello AL, Buonaguro L, Buonaguro FM. Human oncoviruses and p53 tumor suppressor pathway deregulation at the origin of human cancers. Cancers. Jun. 22, 2018;10(7):213. (Year: 2018).*

Hirose M, Yamato K, Endo S, Saito R, Ueno T, Hirai S, Suzuki H, Abei M, Natori Y, Hyodo I. MDM4 expression as an indicator of TP53 reactivation by combined targeting of MDM2 and MDM4 in cancer cells without TP53 mutation. Oncoscience. 2014;1(12):830. (Year: 2014).*

Anonymous, "A Phase 1 Dose-Escalation and Exploratory Dose Expansion Study of AMG 232 in Combination With Carfilzomib, Lenalidomide, and Dexamethasone in Relapsed and/or Refractory Myeloma—History of Changes for Study: NCT03031730", ClinicalTrials.gov Archive, Jul. 31, 2018.

Hirose et al., "MDM4 expression as an indicator of TP53 reactivation by combined targeting of MDM2 and MDM4 in cancer cells without TP53 mutation", *Oncoscience* 1.12: 830 (2014).

Houben et al., "Mechanisms of p53 restriction in Merkel cell carcinoma cells are independent of the Merkel cell polyoma virus T antigens." *Journal of Investigative Dermatology* 133.10: 2453-2460 (2013).

Hu et al., "MDMX overexpression prevents p53 activation by the MDM2 inhibitor Nutlin." *Journal of Biological Chemistry* 281. 44:33030-33035 (2006).

International Search Report & Written Opinion for International Application No. PCT/US2019/058319 dated Feb. 19, 2020.

Liao et al., "The development of piperidinones as potent MDM2-P53 protein-protein interaction inhibitors for cancer therapy", European journal of medicinal chemistry 159: 1-9 (2018).

Lindner et al., "The molecular mechanism of thalidomide analogs in hematologic malignancies," Journal of molecular medicine 94.12: 1327-1334 (2016).

Manni et al., "Inactivation of CK1α in multiple myeloma empowers drug cytotoxicity by affecting AKT and β-catenin survival signaling pathways." *Oncotarget* 8.9: 14604 (2017).

Park et al., "Dual inhibition of MDM2 and MDM4 in virus-positive Merkel cell carcinoma enhances the p53 response." Proceedings of the National Academy of Sciences 116.3 (2019): 1027-1032.

Secchiero et al., "Recent advances in the therapeutic perspectives of Nutlin-3", Current pharmaceutical design 17.6: 569-577 (2011).

Stahl et al., "Lenalidomide use in myelodysplastic syndromes: Insights into the biologic mechanisms and clinical applications", Cancer 123.10: 1703-1713 (2017).

Toledo et al., "MDM2 and MDM4: p53 regulators as targets in anticancer therapy", The international journal of biochemistry & cell biology 39.7-8: 1476-1482 (2007).

* cited by examiner

METHOD OF TREATMENT OF P53 WT TUMORS

RELATED APPLICATIONS AND SUPPORT

This application claims priority to and the benefits of U.S. provisional application 62/752,382 filed Oct. 30, 2018, the content of which is hereby incorporated by reference in its entirety.

This invention was made with government support under grant numbers R01 CA063113 R01 CA173023 and P01 CA203655 awarded by The National Institutes of Health. The government has certain rights in the invention.

FIELD OF THE INVENTION

The present invention relates to methods of treating p53 wild type (WT) tumors. In particular, the invention provides novel therapies for p53 WT tumors based on the combination of an Mouse Double Minute 2 (MDM2) inhibitor together with a Casein Kinase 1 alpha (CK1α) degrading agent and/or an MDM4 inhibitor.

BACKGROUND

Merkel cell carcinoma (MCC) is an aggressive neuroendocrine carcinoma of the skin with an incidence in the United States that has tripled in the last two decades[1, 2]. In 2008, Feng et al. discovered Merkel cell polyomavirus (MCV, MCPy V) clonally integrated in 8 of 10 MCC tumors[3]. MCV positive MCC contains integrated copies of the MCV genome and expresses small T antigen (ST) and a truncated form of large T antigen (LT)[4]. MCC tumor associated truncated LT retains the N-terminal LXCXE, RB-binding motif, but deletes the C-terminal DNA-binding and helicase domains required for viral replication[3]. Expression of MCV ST and truncated LT can promote proliferation and transformation in several cell types, consistent with their oncogenic roles in MCC[5].

The prototypic polyomavirus Simian vacuolating virus 40 (SV40) LT binds to the Retinoblastoma-associated protein RB (RB1) and the cellular tumor antigen p53 (TP53) and inactivates their tumor suppressive functions[6]. In contrast, MCV LT binds to RB but not p53[6]. Next generation sequencing of MCC reveals that virus-negative MCC typically harbors p53 and RB mutations along with a UV damage signature[7, 8]. In contrast, virus-positive MCC usually contains wild type RB and p53 and no evidence for UV damage[7, 8]. Given the presence of wild type p53 in virus-positive MCC, the present inventors suspected that MCV T antigens could functionally inactivate p53 activity.

p53 is mutated in a wide variety of cancers. Alternatively, wild type p53 can be functionally inactivated by overexpression of MDM2, a ubiquitin ligase targeting p53, or MDM4 (MDMX)[9, 10]. MDM2 and MDM4 both have similar structures with N-terminal p53 binding and C-terminal RING domains[11]. Although MDM4 does not directly ubiquitinate p53, its RING domain facilitates recruitment of ubiquitin to MDM2[11]. MDM4 also has an auto-inhibitory domain that reduces binding to p53[12]. The MDM4 auto-inhibitory interaction can be relieved by Casein kinase 1 alpha (CK1 a, CSNK1A1)[13].

SUMMARY OF THE INVENTION

The present invention provides novel combinations comprising an MDM2 inhibitor and Casein Kinase 1 alpha (CK1α) degrading agent and/or an MDM4 inhibitor for use in treating a p53 WT tumor in a subject.

In the combinations according to the present invention, the MDM2 inhibitor may be selected from the group consisting of nutlin-3, idasanutlin (RG7388, RO5503781, Roche), RG7775 (RO6839921, Roche), RO5045337 (Roche), AMG232 (Amgen), DS3032 (DS3032b, Daiichi Sankyo), ALRN-6924 (Aileron), KRT-232 (Kartos), ATSP-7041, CGM097 (Novartis), and HDM201 (Novartis), preferably is HDM201, i.e. (S)-5-(5-Chloro-1-methyl-2-oxo-1, 2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one.

In the combinations according to the present invention, the Casein Kinase 1 alpha (CK1α) degrading agent and/or an MDM4 inhibitor be selected from the group consisting of thalidomide, pomalidomide, lenalidomide and SC-24-UR99 (Novartis), i.e. 4-(3-amino-1-(4-chloro-5-methyl-6-(methylamino)pyridin-3-yl)-5-fluoro-1H-indazol-6-yl)naphthalen-1-ol, preferably is lenalidomide, i.e. (RS)-3-(7-Amino-3-oxo-1H-isoindol-2-yl)piperidin-2,6-dion, also referred to as REVLIMID.

The present inventions provide such combinations in particular with the MDM2 inhibitor HDM201 and the CK1α degrading agent lenalidomide.

The combinations according to the present invention may comprise further anti-cancer agent(s).

Further anti-cancer agents according to the present invention may be selected from:
- FLT3 inhibitors (e.g. gilterinib, quizartinib, midostaurin),
- BCL2 inhibitors (e.g. navitoclax, venetoclax),
- other MDM2 inhibitors (e.g. nutlin-3, idasanutlin, AMG232, DS-3032B, ALRN6924/ATSP7041),
- hypomethylating agents (HMA) (e.g. Vidaza [azacytidine, 5-azacytidine], Dacogen [decitabine], guadecitabine),
- anthracyclines (e.g. idarubicin, daunorubicin, doxorubicin, epirubicin);
- anti-CD33 antibodies (e.g. Mylotarg [gemtuzumab], vadastuximab)
- and other agents (e.g. AraC [cytarabine, aracytine]).

P53 WT tumors which may be treated by the combinations in accordance with the present invention may be solid tumors or hematological tumors. Solid tumor may be sarcomas, e.g. liposarcoma or soft tissue sarcoma, lymphomas, e.g. non-Hodgkin's lymphoma (NHL), in particular, Mantle cell lymphoma (MCL), melanomas, e.g. skin melanoma or uveal melanoma, blastomas (e.g. neuroblastoma), colon tumor, colorectal tumor, kidney tumor, and liver tumor or skin cancer, e.g. Merkel cell carcinoma (MCC), in particular Merkel cell polyomavirus (MCV) positive MCC. Hematological tumor may be acute myeloid leukemia (AML), multiple myeloma (MM), myelodysplastic syndrome (MDS), or acute lymphoblastic leukemia (ALL).

In particular, the present invention provides the following embodiments:

1. A combination comprising (a) an mouse double minute 2 (MDM2) inhibitor and (b) a Casein Kinase 1 alpha (CK1α) degrading agent and/or a mouse double minute 4 (MDM4) inhibitor.

2. A combination comprising (a) an MDM2 inhibitor and (b) a CK1a degrading agent and/or an MDM4 inhibitor for use in treating a p53 wild type (WT) tumor in a subject.

3. A method of treating a p53 WT tumor in a subject, comprising administering to the subject a combination of (a) an MDM2 inhibitor and (b) a CK1a degrading agent and/or an MDM4 inhibitor.

4. The combination of embodiment 1, the combination for use of embodiment 2, or the method of embodiment 3, wherein the MDM2 inhibitor is selected from the group consisting of nutlin-3, idasanutlin (RG7388, RO5503781), RG7775 (RO6839921), AMG232, DS3032 (DS3032b), ALRN-6924, ATSP-7041, CGM097, and HDM201, i.e. (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one.

5. The combination of embodiment 1, the combination for use of embodiment 2, or the method of embodiment 3, wherein the MDM2 inhibitor is selected from the group consisting of nutlin-3, idasanutlin, and HDM201.

6. The combination of embodiment 1, the combination for use of embodiment 2, or the method of embodiment 3, wherein the MDM2 inhibitor is HDM201.

7. The combination of any one of embodiments 1, 4-6, the combination for use of any one of embodiments 2, 4-6, or the method of any one of embodiments 3-6, wherein the CK1α degrading agent and/or an MDM4 inhibitor is selected from the group consisting of thalidomide, pomalidomide, lenalidomide i.e. (RS)-3-(7-Amino-3-oxo-1H-isoindol-2-yl)piperidin-2,6-dion, also referred to as REVLIMID, and SC-24-UR99, i.e. 4-(3-amino-1-(4-chloro-5-methyl-6-(methylamino)pyridin-3-yl)-5-fluoro-1H-indazol-6-yl)naphthalen-1-ol.

8. The combination of any one of embodiments 1, 4-6, the combination for use of any one of embodiments 2, 4-6, or the method of any one of embodiments 3-6, wherein the CK1α degrading agent and/or an MDM4 inhibitor is selected from the group consisting of lenalidomide and SC-24-UR99.

9. The combination of embodiment 1, the combination for use of embodiment 2, or the method of embodiment 3, wherein the MDM2 inhibitor is selected from the group consisting of nutlin-3, idasanutlin, and HDM201, and wherein the CK1α degrading agent and/or an MDM4 inhibitor is selected from the group consisting of lenalidomide and SC-24-UR99.

10. The combination of embodiment 1, the combination for use of embodiment 2, or the method of embodiment 3, wherein the MDM2 inhibitor is HDM201, and the CK1α degrading agent and/or an MDM4 inhibitor is lenalidomide.

11. The combination for use of any one of embodiments 2, 4-10, or the method of any one of embodiments 3-10, wherein the p53 WT tumor is a solid tumor.

12. The combination for use of embodiment 11, or the method of any one of embodiment 11, wherein the solid tumor is selected from the group consisting of sarcomas, e.g. liposarcoma or soft tissue sarcoma, lymphomas, e.g. non-Hodgkin's lymphoma (NHL), in particular, Mantle cell lymphoma (MCL), melanomas, e.g. skin melanoma or uveal melanoma, blastomas (e.g. neuroblastoma), colon tumor, colorectal tumor, kidney tumor, liver tumor and skin cancer, e.g. Merkel cell carcinoma (MCC).

13. The combination for use of embodiment 11, or the method of embodiment 11, wherein the solid tumor is a Merkel cell carcinoma (MCC).

14. The combination for use of embodiment 13, or the method of embodiment 13, wherein the Merkel cell carcinoma (MCC), is a Merkel cell polyomavirus (MCV)-positive MCC.

15. The combination for use of any one of embodiments 2, 4-10, or the method of any one of embodiments 3-10, wherein the p53 WT tumor is a hematological tumor (or a hematologic malignancy).

16. The combination for use of embodiment 15, or the method of embodiment 15, wherein the hematological tumor is selected from the group consisting of acute myeloid leukemia (AML), multiple myeloma (MM), myelodysplastic syndrome (MDS), and acute lymphoblastic leukemia (ALL).

17. The combination for use of embodiment 15, or the method of embodiment 15, wherein the hematological tumor is selected from the group consisting of multiple myeloma (MM), and myelodysplastic syndrome (MDS).

18. The combination for use of embodiment 15, or the method of embodiment 15, wherein the hematological tumor is myelodysplastic syndrome (MDS).

19. The combination for use of embodiment 2, or the method of embodiment 3, wherein the MDM2 inhibitor is HDM201, wherein the CK1α degrading agent and/or an MDM4 inhibitor is lenalidomide, and wherein the p53 WT tumor is MCV-positive MCC.

20. The combination for use of embodiment 2, or the method of embodiment 3, wherein the MDM2 inhibitor is HDM201, wherein the CK1α degrading agent and/or an MDM4 inhibitor is lenalidomide, and wherein the p53 WT tumor is MDS.

21. The combination of/the combination for use of/the method of any one of the preceding embodiments, further comprising one or more further anti-cancer agent(s).

The combinations described herein can provide a beneficial anti-cancer effect, e.g., an enhanced anti-cancer effect, reduced toxicity, and/or reduced side effects. For example, a first therapeutic agent, e.g., any of the therapeutic agents disclosed herein, and a second therapeutic agent, e.g., the one or more additional therapeutic agents, or all, can be administered at a lower dosage than would be required to achieve the same therapeutic effect compared to a monotherapy dose. Thus, compositions and methods for treating proliferative disorders, including cancer, using the aforesaid combination therapies are disclosed.

In some embodiments, a method of treating a subject, e.g., a subject having a cancer described herein, with a combination described herein, comprises administration of a combination as part of a therapeutic regimen. In an embodiment, a therapeutic regimen comprises one or more, e.g., two, three, or four combinations described herein. In some embodiments, the therapeutic regimen is administered to the subject in at least one phase, and optionally two phases, e.g., a first phase and a second phase. In some embodiments, the first phase comprises a dose escalation phase. In some embodiments, the first phase comprises one or more dose escalation phases, e.g., a first, second, or third dose escalation phase. In some embodiments, the dose escalation phase comprises administration of a combination comprising two, three, four, or more therapeutic agents, e.g., as described herein. In some embodiments, the second phase comprises a dose expansion phase. In some embodiments, the dose expansion phase comprises administration of a combination comprising two, three, four, or more therapeutic agents, e.g., as described herein. In some embodiments, the dose expansion phase comprises the same two, three, four, or more therapeutic agents as the dose escalation phase.

In some embodiments, the first dose escalation phase comprises administration of a combination comprising two therapeutic agents, e.g., two therapeutic agents described herein, wherein a maximum tolerated dose (MTD) or recommended dose for expansion (RDE) for one or both of the therapeutic agents of is determined. In some embodiments, prior to the first dose escalation phase, the subject was administered with one of the therapeutic agents administered in the first dose escalation phase as a single agent.

In some embodiments, the second dose escalation phase comprises administration of a combination comprising three therapeutic agents, e.g., three therapeutic agents described herein, wherein a maximum tolerated dose (MTD) or recommended dose for expansion (RDE) for one, two, or all of the therapeutic agents is determined. In some embodiments, the second dose escalation phase starts after the first dose escalation phase ends. In some embodiments, the second dose escalation phase comprises administration of one or more of the therapeutic agents administered in the first dose escalation phase. In some embodiments, the second dose escalation phase is performed without performing the first dose escalation phase.

In some embodiments, the third dose escalation phase comprises administration of a combination comprising four therapeutic agents, e.g., four therapeutic agents described herein, wherein a maximum tolerated dose (MTD) or recommended dose for expansion (RDE) of one, two, three, or all of the therapeutic agents is determined. In some embodiments, the third dose escalation phase starts after the first or second dose escalation phase ends. In some embodiments, the third dose escalation phase comprises administration of one or more (e.g., all) of therapeutic agents administered in the second dose escalation phase. In some embodiments, the third dose escalation phase comprises administration of one or more of the therapeutic agents administered in the first dose escalation phase. In some embodiments, the third dose escalation phase is performed without performing the first, second, or both dose escalation phases.

In some embodiments, the dose expansion phase starts after the first, second or third dose escalation phase ends. In some embodiments, the dose expansion phase comprises administration of a combination administered in the dose escalation phase, e.g., the first, second, or third dose escalation phase. In an embodiment, a biopsy is obtained from a subject in the dose expansion phase.

Without wishing to be bound by theory, it is believed that in some embodiments, a therapeutic regimen comprising a dose escalation phase and a dose expansion phase allows for entry of new agents or regiments for combination, rapid generation of combinations, and/or assessment of safety and activity of tolerable combinations.

Here, the present inventors demonstrate that MCV ST functions as a transcriptional activator to increase levels of MDM2 and CK1α that in turn cooperate with MDM4 to inhibit p53 function in MCC. The present inventors further demonstrate the synergistic efficacy of targeting both MDM2 and MDM4 in MCC.

Merkel cell carcinoma (MCC) is an aggressive skin cancer. While virus-negative (Merkel cell polyomavirus, MCV) MCC contains inactivating mutations in RB and p53, MCV-positive MCC usually contains wild type RB and p53. The present inventors demonstrate that MCV large T antigen binding to RB results in p53 activation, while MCV small T antigen reduces p53 activation by increasing levels of MDM2 and CK1α, an activator of MDM4. Targeted degradation of CK1α by lenalidomide or a specific MDM4 inhibitor acts synergistically with MDM2 inhibitors to activate p53 and induce apoptosis. The present inventors' work uncovers the mechanism behind MCV control of p53 in MCC and demonstrates the utility of targeting MDM2 and MDM4 combinatorically in p53 wild type tumors.

Merkel cell polyomavirus (MCV) contributes to approximately 80% of all Merkel cell carcinomas (MCC), a highly aggressive neuroendocrine carcinoma of the skin. MCV-positive MCC expresses small T antigen (ST) and a truncated form of large T antigen (LT) and usually contains wild type p53 (TP53) and RB (RB1). In contrast, virus-negative MCC contains inactivating mutations in TP53 and RB1. While the MCV truncated LT can bind and inhibit RB, it does not bind p53. The present inventors disclose here that MCV LT binds to RB leading to increased levels of ARF, an inhibitor of MDM2, and activation of p53. However, co-expression of ST reduced p53 activation.

MCV ST recruits the MYC homologue MYCL (L-Myc) to the EP400 chromatin remodeler complex and transactivates specific target genes. The present inventors observed that depletion of EP400 in MCV-positive MCC cell lines led to increased p53 target gene expression. The present inventors suspected that the MCV ST-MYCL-EP400 complex could functionally inactivate p53 but the underlying mechanism was not known. Integrated ChIP and RNA-seq analysis following EP400 depletion identified MDM2 as well as CK1α, an activator of MDM4, as target genes of the ST-MYCL-EP400 complex. In addition, MCV-positive MCC cells expressed high levels of MDM4. Combining MDM2 inhibitors with lenalidomide targeting CK1α or an MDM4 inhibitor caused synergistic activation of p53 leading to an apoptotic response in MCV-positive MCC cells and MCC-derived xenografts in mice. These results support dual targeting of MDM2 and MDM4 in virus-positive MCC and other p53 wild type tumors.

Figure 1A:
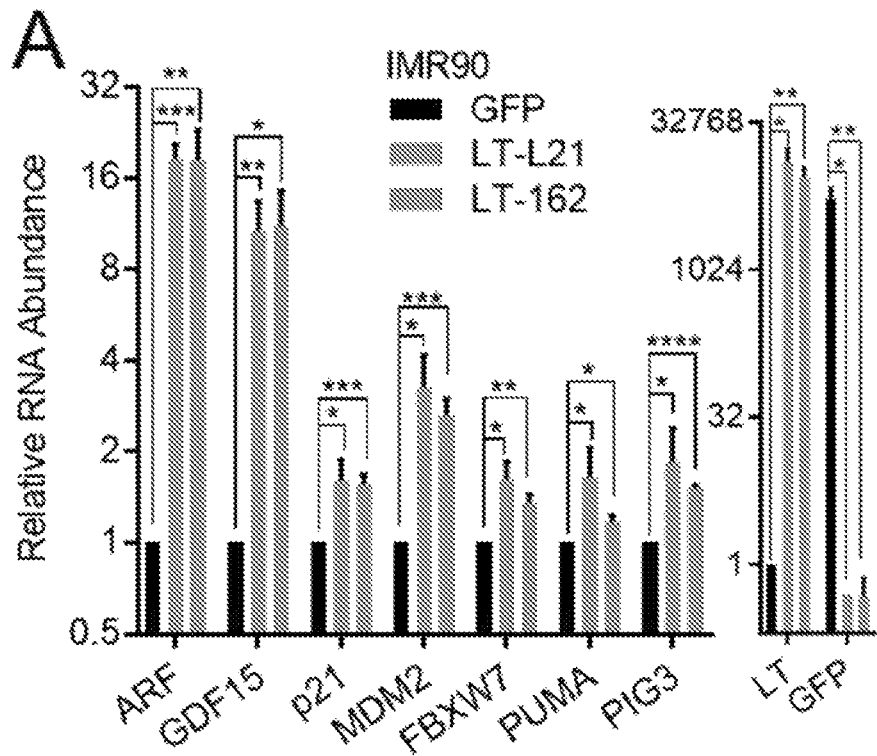
FIG. 1. Merkel cell polyomavirus large T antigen activates and small T antigen dampens the p53 response.

A. Inducible expression of truncated tumor isoforms of MCV LT increases ARF and p53 target genes in IMR90 cells. Expression of GFP or LT-L21 and LT-162 truncated LT, was induced with doxycycline (DOX) treatment for 24 hours. The LT, ARF and p53 target gene RNA levels were normalized to those of the GFP induced cells, whereas the GFP levels were normalized to the LT-L21 samples. Data are shown as mean±SD; *student t-test $P<0.05$, $P<0.005$, *$P<0.0005$, ****$P<0.00005$.

B. IMR90 cells were induced to express GFP, ST, LT-L21 or LT-L21 with ST for 40 hours. Lysates were prepared before (−) or after (+) DOX. Activation of p53 response is reflected by increased levels of p53, phospho-Serine 15 p53 (P-p53), acetyl-lysine 382 p53 (Ac-p53), p21 and cleaved PARP (**).

C. Expression of L21 but not an LT mutant in the LXCXE motif (E216K) activates p53 through inhibiting RB and inducing ARF.

FIG. 2. MDM2 and CK1a are transcriptional targets of the ST-MYCL-EP400 complex.

A. Volcano plot illustrating differentially expressed p53 target genes in MKL-1 MCC cell lines after depletion of EP400 with inducible shRNA relative to control shRNA. Each gene log 2 fold change was plotted against −log 10 p-value for statistical significance. Green dots indicate genes that meet the 2-fold change cutoff and red dots signify adjusted p-value less than 0.1.

B. RT-qPCR was performed with MKL-1 cells after shRNA was induced for 8 days. Reads were normalized to RPLP0 and un-induced samples. The experiment was performed three times and averaged. Data are shown as mean±SD; *student t-test $P<0.05$, $P<0.005$, *$P<0.0005$, ****$P<0.00005$.

C. ChIP with MAX, EP400, ST and IgG antibodies followed by qPCR of indicated promoters in MKL-1 cells. ChIP-qPCR was performed three times with average percent input shown.

D. Depletion of MCV T antigens causes a reduction in the MDM2, CK1α and MDM4 levels. MKL-1 cells were transduced with specific shRNAs for five days and harvested for western blotting.

E. ChIP-qPCR with MAX, EP400 and ST antibodies for the MDM2 promoter in IMR90 cells in the presence (+) or absence (−) of MCV T antigens. ChIP was performed five times independently.

F. Nutlin-3 treatment does not elicit p53 response, but MCV T antigens increase levels of MDM2, MDM4 and CK1α in IMR90 cells expressing p53DD. MKL-1 and IMR90-p53DD were treated with Nutlin-3(1 μM) for 24 hours.

FIG. 3. MDM4 is overexpressed in MCV-positive MCC.

A. RNA from MCC cell lines and human foreskin fibroblasts (HFF) was harvested for RT-qPCR for MDM4 (total), MDM4-FL (full-length variant), and MDM4-S (short splice variant). MDM4 levels were normalized with the geomean of RPLP0, 18s rRNA and beta-actin RNA controls. Data are shown as mean±SD; *student t-test P<0.05 for MDM4-FL.

B. Western blot of MCC cell lines and HFF with indicated antibodies. MS-1 and MCC13 overexpress p53 due to inactivating mutations and MKL-2 and MCC26 do not express detectable levels of p53.

FIG. 4. Inhibition of MDM2 and MDM4 enhances p53 activation in MCC cell lines.

A. Lenalidomide enhances p53 activation by nutlin-3 in MKL-1. MKL-1 cells were treated with nutlin-3 (5 μM), lenalidomide (Len, 10 μM) or both for 40 hours.

B. Lenalidomide depletes CK1α, but it does not enhance p53 activation by nutlin-3 in UISO cells. MKL-1 (MCV+ MCC) or UISO (MCV− MCC) cells were treated with nutlin-3 (1 μM) with or without lenalidomide (10 μM) for 24 hours. Of note, UISO has less MDM2 and MDM4 proteins than MKL-1.

C. Lenalidomide and to a lesser degree pomalidomide but not thalidomide, cooperate with nutlin-3 to activate p53. MKL-1 cells were treated with nutlin-3 with lenalidomide, pomalidomide (10 μM) or thalidomide (10 μM) for 24 hours.

D. Lenalidomide treatment reduces MDM4 binding to p53 and activated MDM2. MKL-1 cells were treated with nutlin-3 (5 μM), lenalidomide (10 μM) or both for 40 hours and harvested for immunoprecipitation with antibodies to MDM4, p53 and CK1α followed by western blotting.

E. Depletion of CK1α by CRISPR transduction enhances p53 activation by nutlin-3. MKL-1 cells stably expressing each of two CK1α sgRNAs were treated with nutlin-3 (1 μM) with or without lenalidomide for 24 hours. Lenalidomide further decreased CK1α that sgRNAs did not completely deplete.

F. MDM4 inhibitor SC-24-UR99 (UR99) cooperates with MDM2 inhibitors in activating p53. MKL-1 cells were treated with nutlin-3 (1 μM) or HDM201 (0.1 μM) with or without lenalidomide (1 μM) or UR99 (0.1 μM).

FIG. 5. Inhibition of MDM2 and CK1α-MDM4 synergistically induces cell death by apoptosis.

A. MKL-1 and MS-1 cells were treated with MDM2 inhibitors, nutlin-3, RG7388 or AMG232 at several concentrations and XTT assay was performed after 96 hours of treatment. **multiple t-test p-value<0.005.

B. Bliss synergy test displays a strong synergy between nutlin-3 and lenalidomide or SC-24-UR99 but not with thalidomide.

C. BH3 profiling was performed with MKL-1 cells treated with lenalidomide, nutlin-3 or both drugs for 16 hours. The experiment was performed three times. Data are shown as mean±SD; *student t-test P<0.05.

D. MKL-1 MCC xenografts in SCID mice respond to the combinational treatment of HDM201 and lenalidomide. HDM201 (40 mg/kg), lenalidomide (50 mg/kg) or both drugs were administered orally daily starting when xenograft tumors were 200 mm3. Data are shown as mean±SEM; multiple t-test between HDM201 and combination treatments * P<0.05 #—the study was terminated because the tumor volume reached maximum permissible size.

E. Model: Merkel cell polyomavirus T antigens sensitize Merkel cell carcinoma for targeting the p53-MDM2-MDM4 pathway.

Figure 6A:
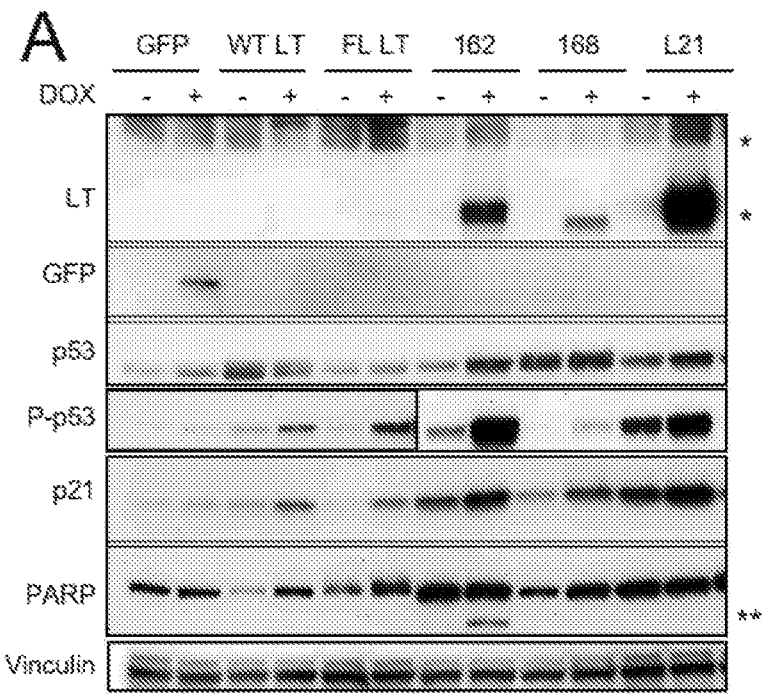
Figure 6B:
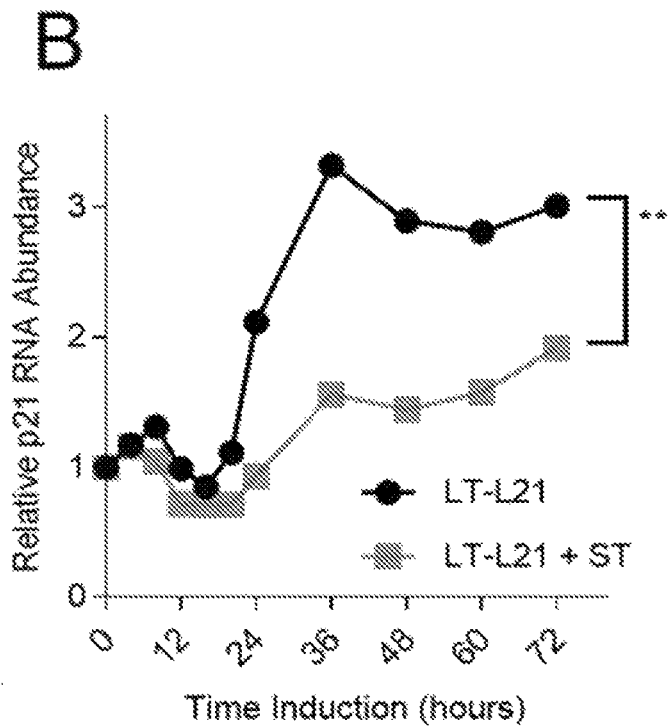
Figure 6C:
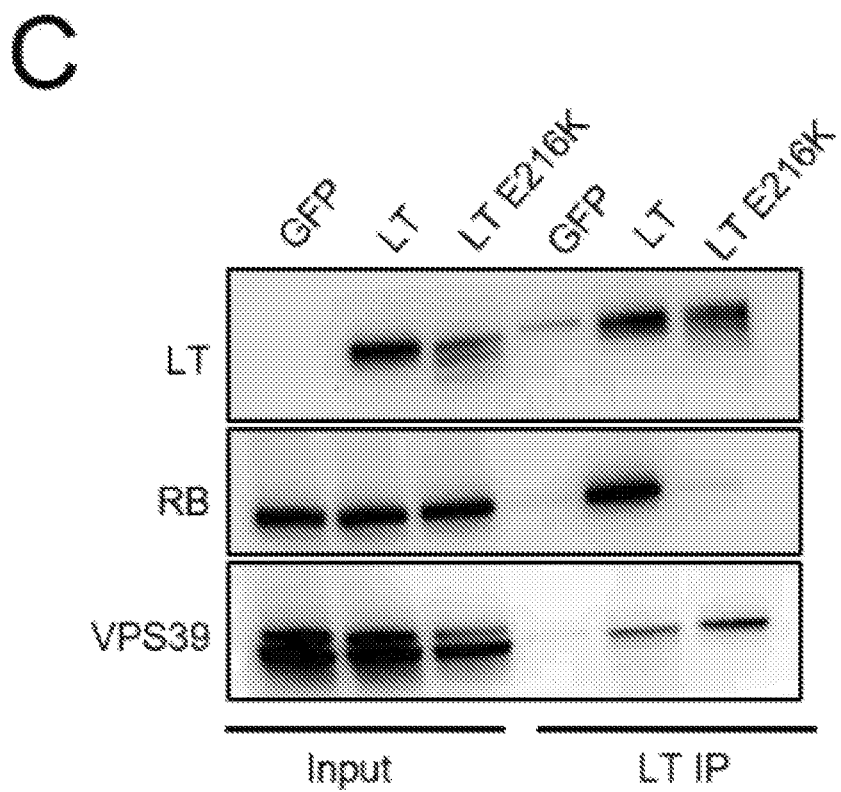
Figure 7A:
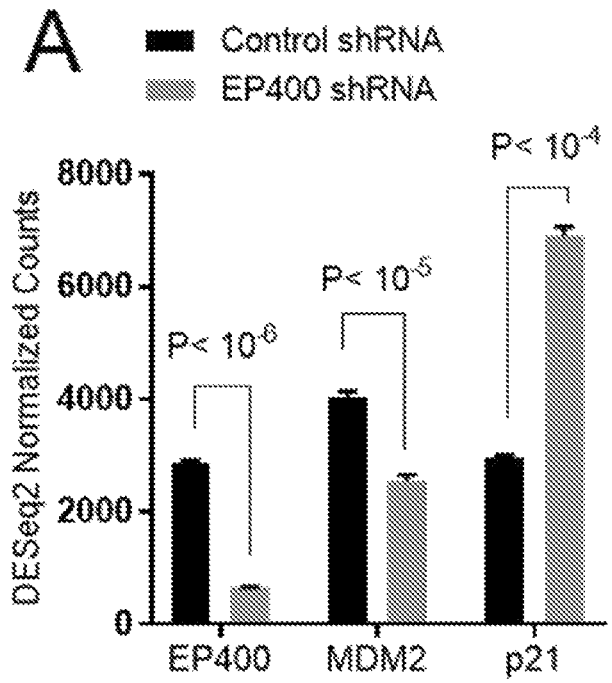
Figure 7B:
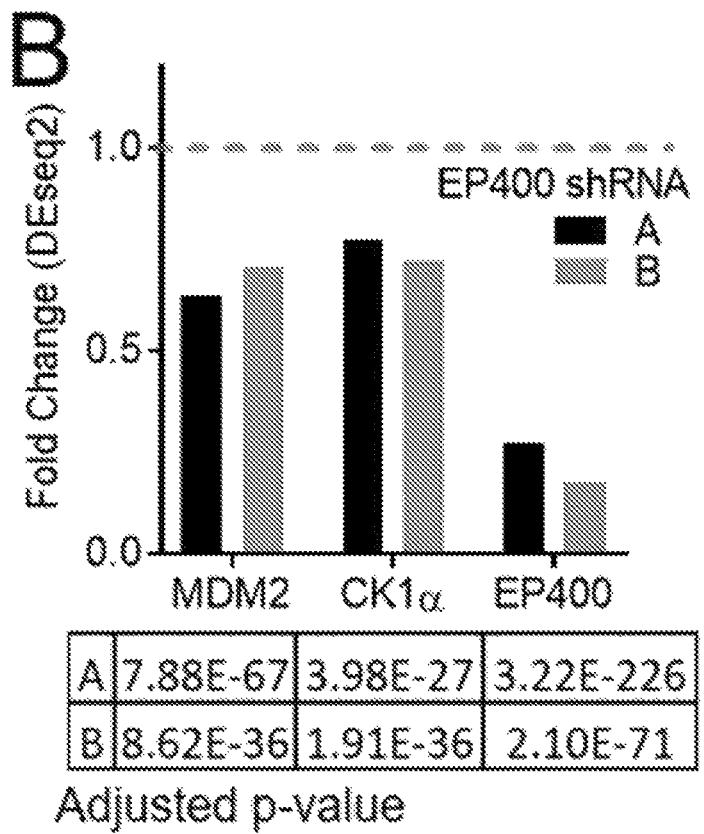
Figure 7C:
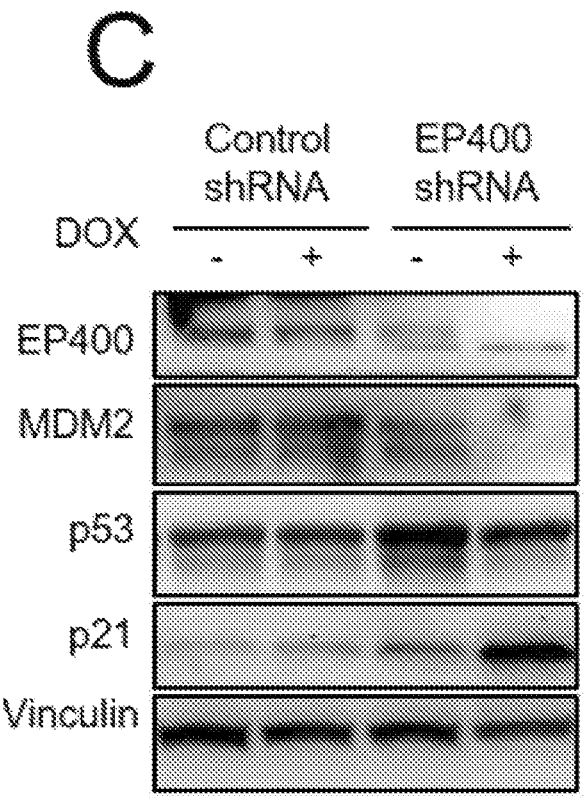
Figure 7D:
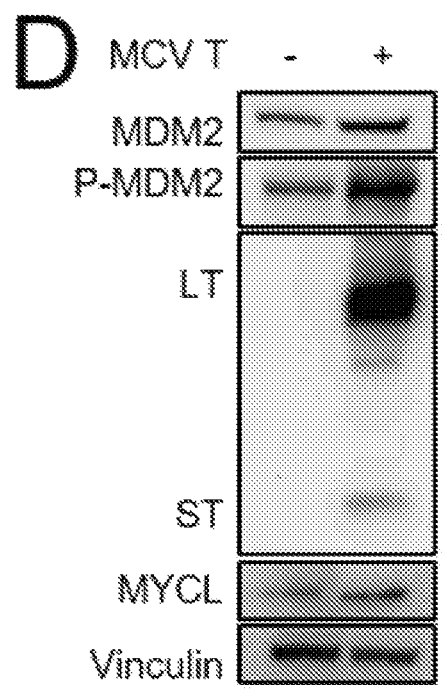
Figure 7E:
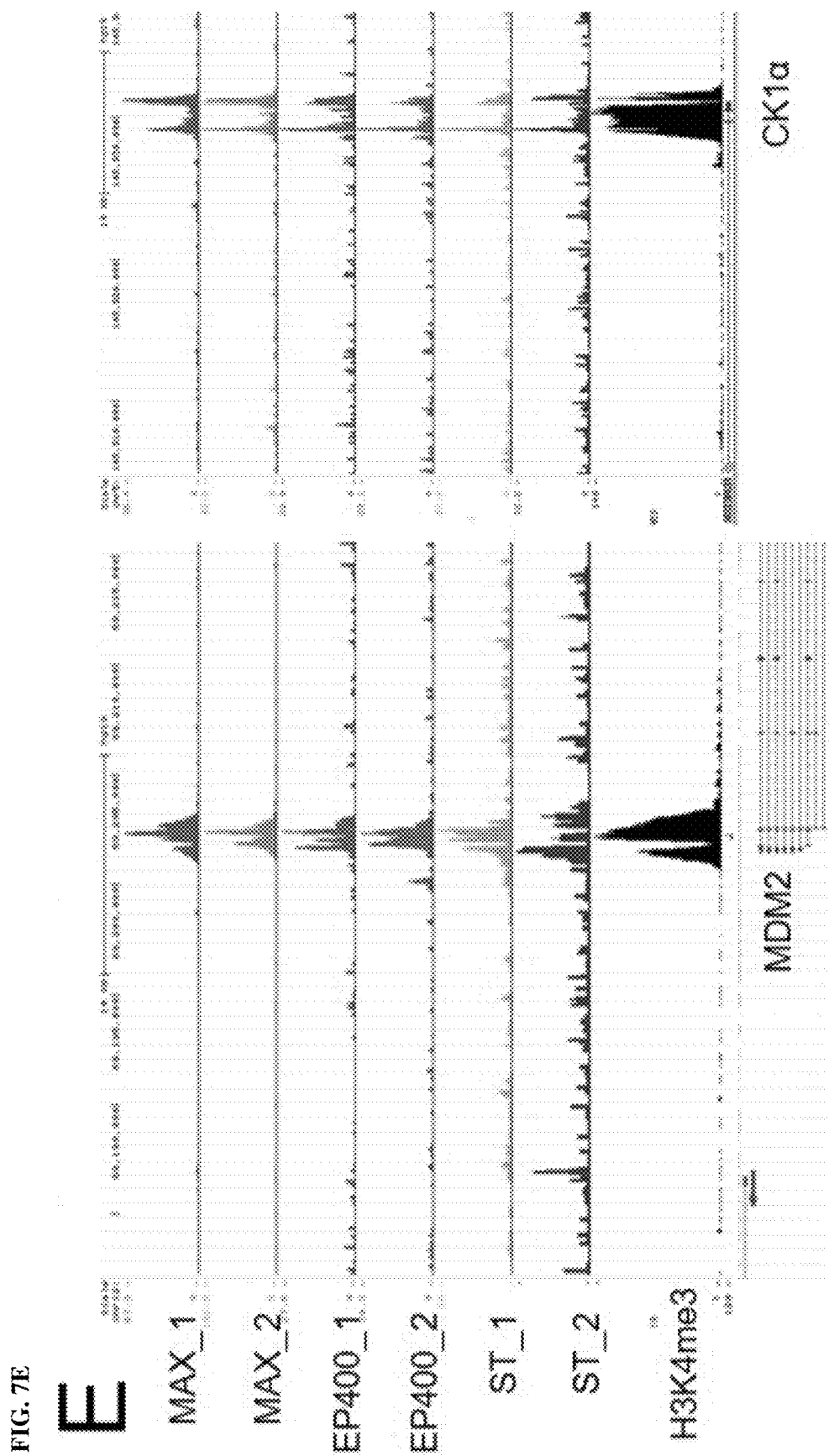
Figure 7F:
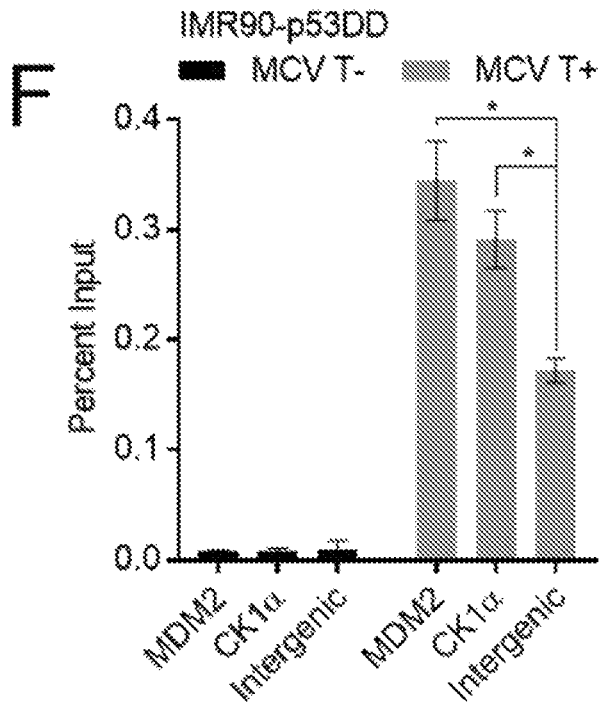
Figure 7G:
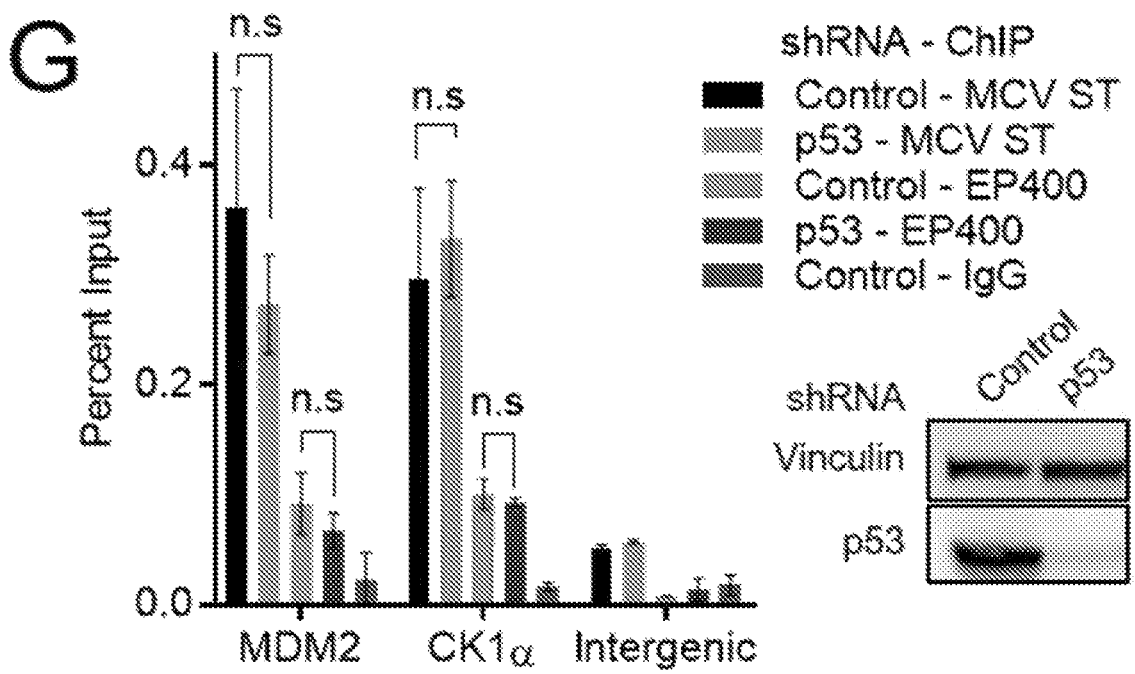

FIG. 6 (herein also referred to as FIG. S1).

A. Inducible expression of full-length or truncated tumor isoforms of MCV LT activates p53 in IMR90 cells. Expression of GFP or WT (wild type) LT, FL (full-length) LT, 162, 168 and L21 truncated LT, was induced with doxycycline (DOX) treatment for 40 hours. Lysates were prepared before (−) or after (+) DOX. Activation of p53 response is reflected by increased levels of p53, phospho-Serine 15 p53 (P-p53), acetyl-lysine 382 p53 (Ac-p53), p21 and cleaved PARP (**).

B. RT-qPCR shows that LT-L21 induction in IMR90 cells increases levels of known p53 target gene p21. L21-LT, either alone or with ST as splice variants, was induced for 4, 8, 12, 16, 20, 24, 36, 48, 60 and 72 hours and RNA was harvested for RT-qPCR. The data shown is a representation of three independent experiments. **two-way ANOVA p-value<0.005.

C. The LXCXE LT mutant can bind to VPS39 but not RB. HCT116 cells stably expressing GFP, LT-L21 or LT-L21 E216K mutant were harvested for LT immunoprecipitation.

FIG. 7 (herein also referred to as FIG. S2).

A. Normalized counts of RNA-seq indicate that levels of MDM2 decreased and p21 increased with EP400 shRNA relative to control shRNA in MKL-1.

B. RNA-seq fold change of MDM2, CK1α (CSNK1A1) and EP400 compared to control shRNA after depleting EP400 using two independent shRNAs displays reduced levels of MDM2 and CK1α along with EP400. Adjusted p-values for Bonferroni correction are shown.

C. MKL-1 cells were induced to express EP400 or control shRNA for 8 days. Western blot shows decreased MDM2 and EP400 levels and increased p53 and p21 levels with EP400 shRNA.

D. IMR90 cells stably expressing hTERT, p53DD, MYCL (IMR90-p53DD) with (+) or without (−) MCV T antigens (LT-L21 and ST) were blotted with indicated antibodies.

E. Two independent ChIP-seq of MAX, EP400 and ST show peaks at the MDM2 and CK1α promoters, also marked by H3K4me3.

F. ChIP-qPCR of ST shows that MCV ST binds to the promoters of the MDM2 and CK1α promoters in IMR90-p53DD cells expressing MCV T antigens. The experiment was performed twice. Data are shown as mean±SD; *P<0.05, n.s>=0.05.

G. ST and EP400 enrich in the MDM2 and CK1α promoters in MKL-1 cells depleted of p53. MKL-1 stably expressing an p53 shRNA was used. The experiment was performed twice.

Figure 8A:
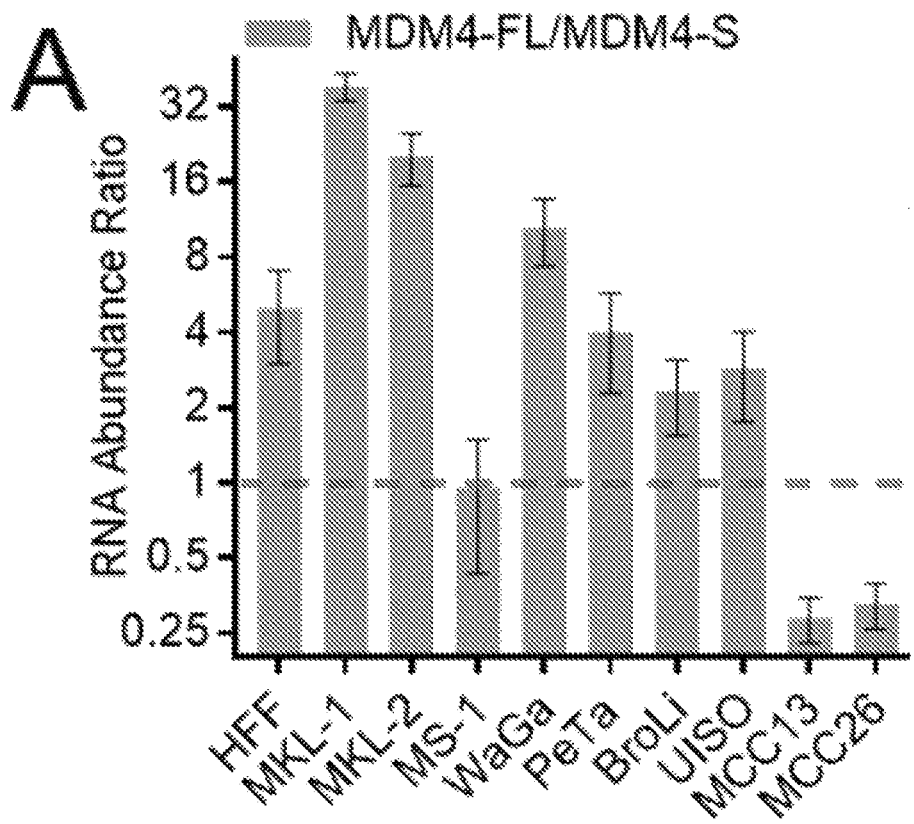
Figure 8B:
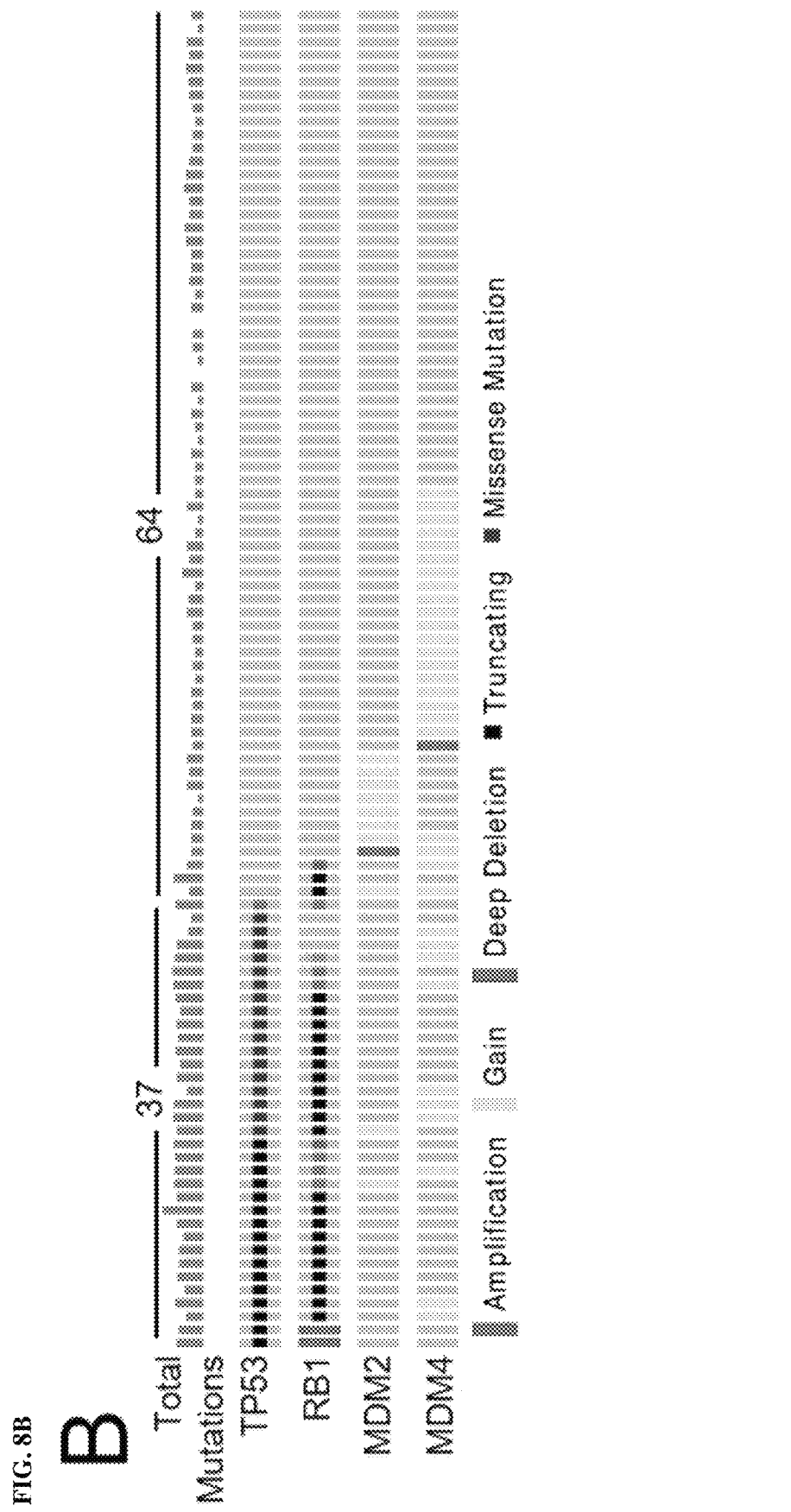
Figure 9A:
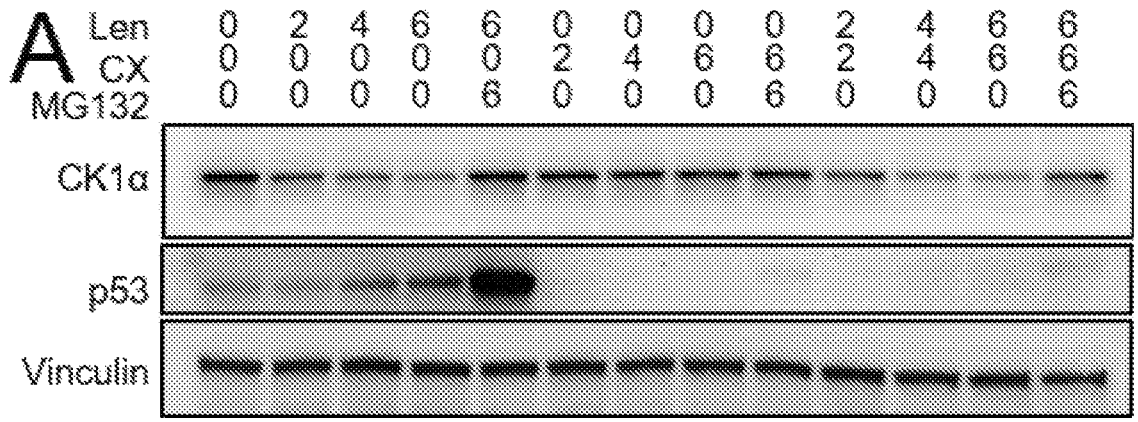
Figure 9B:
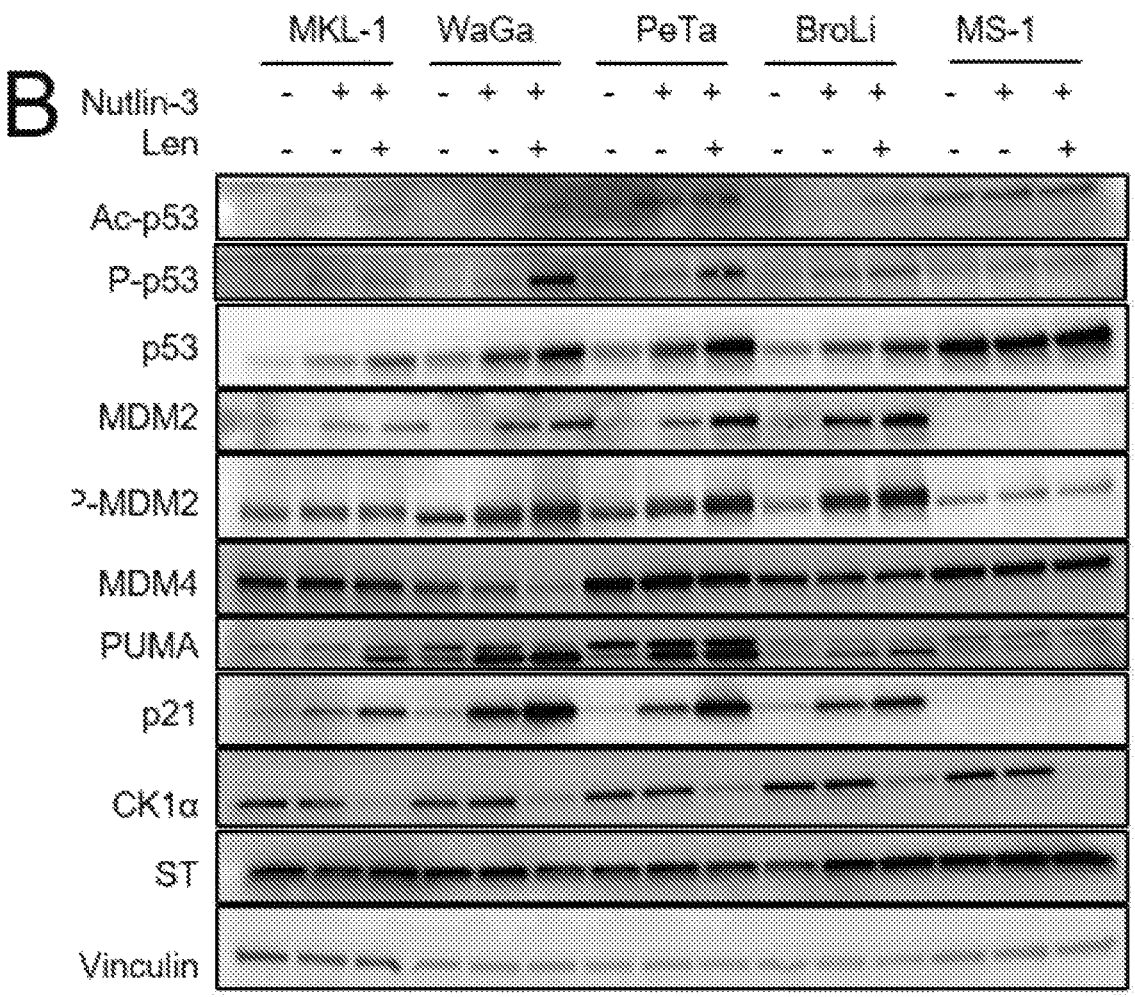
Figure 9C:
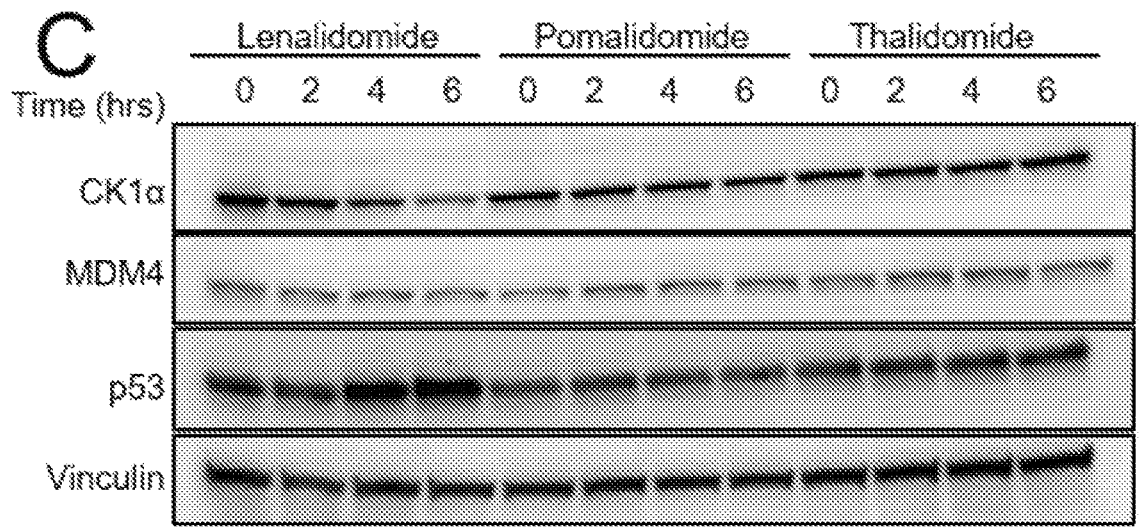
Figure 9D:
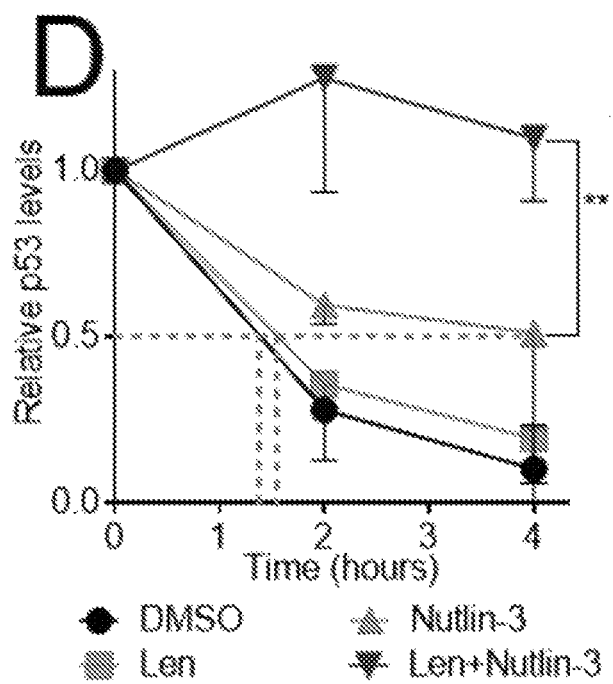
Figure 9E:
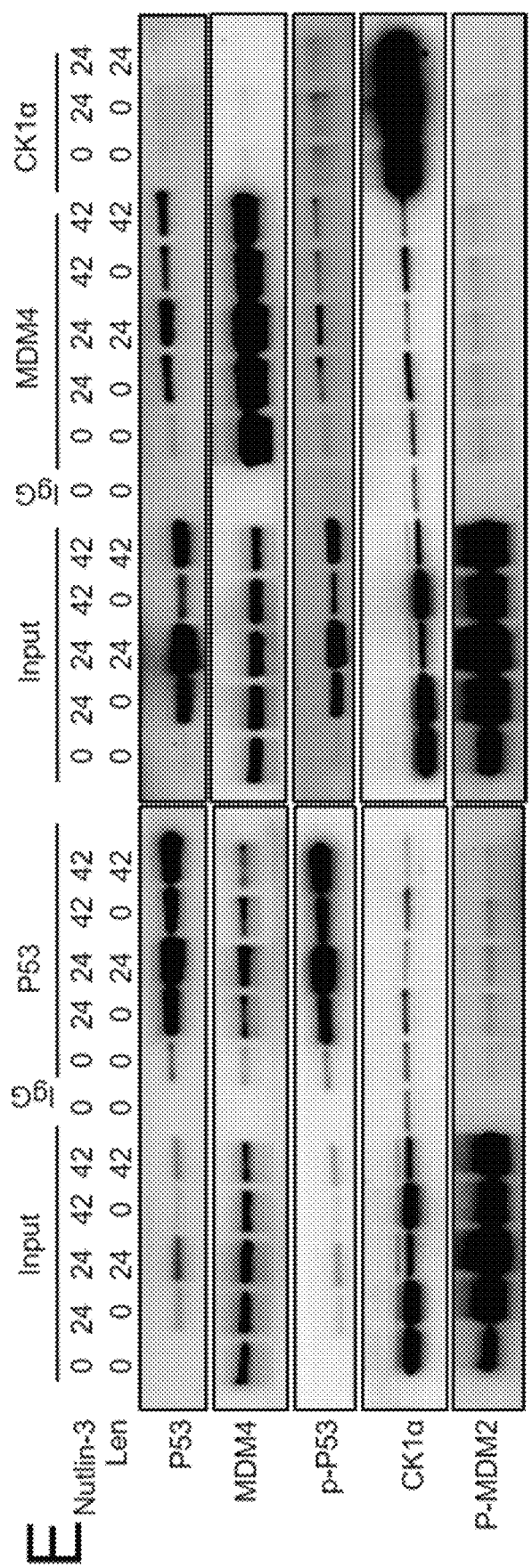
Figure 10A:
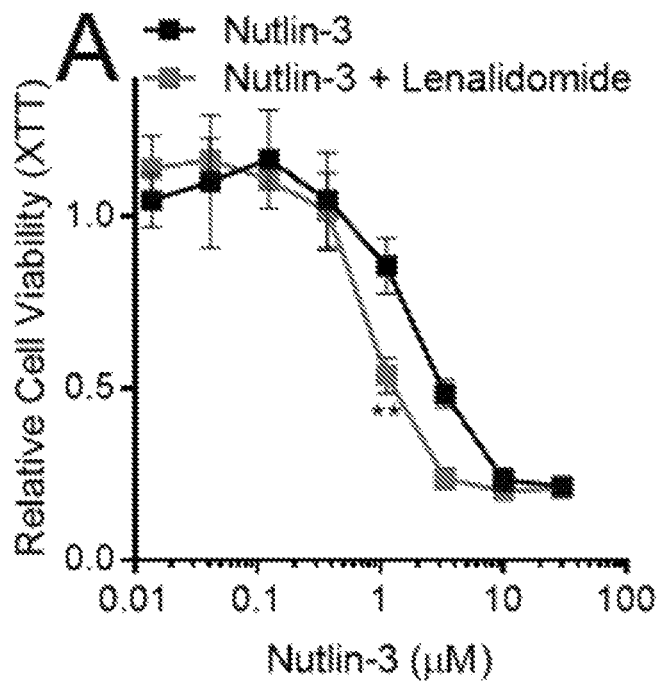
Figure 10B:
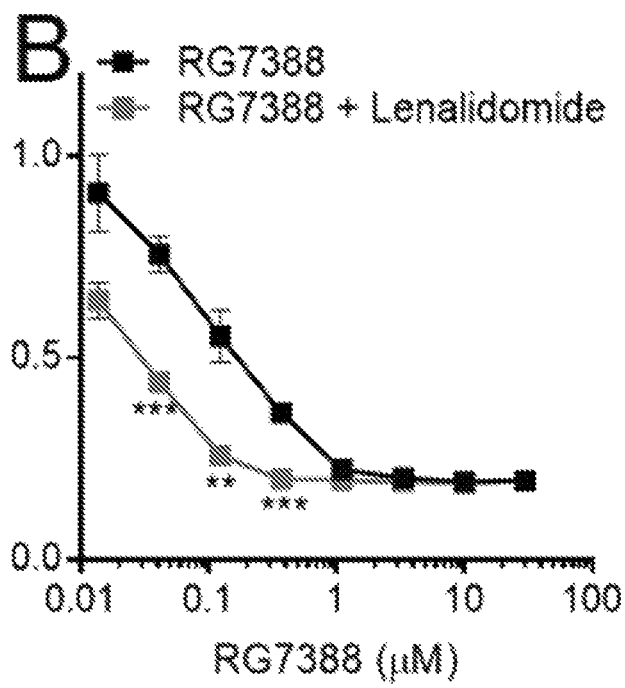
Figure 10C:
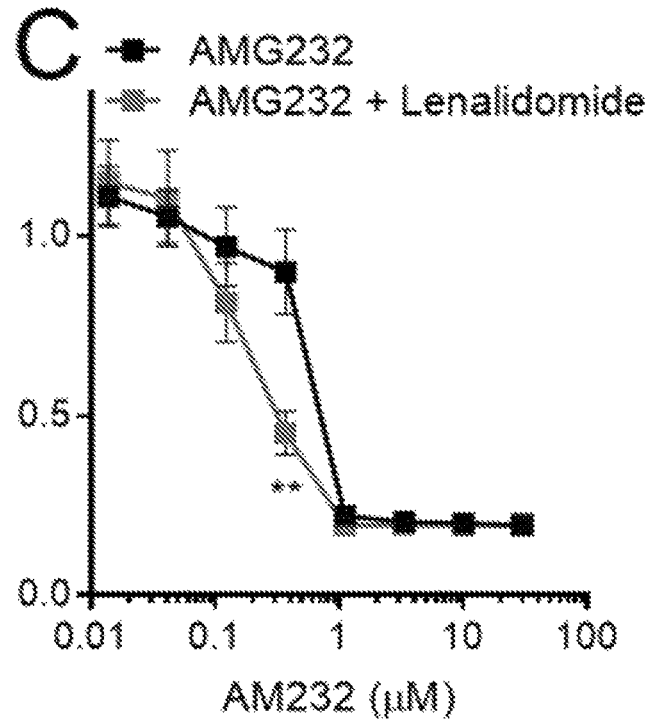
Figure 10D:
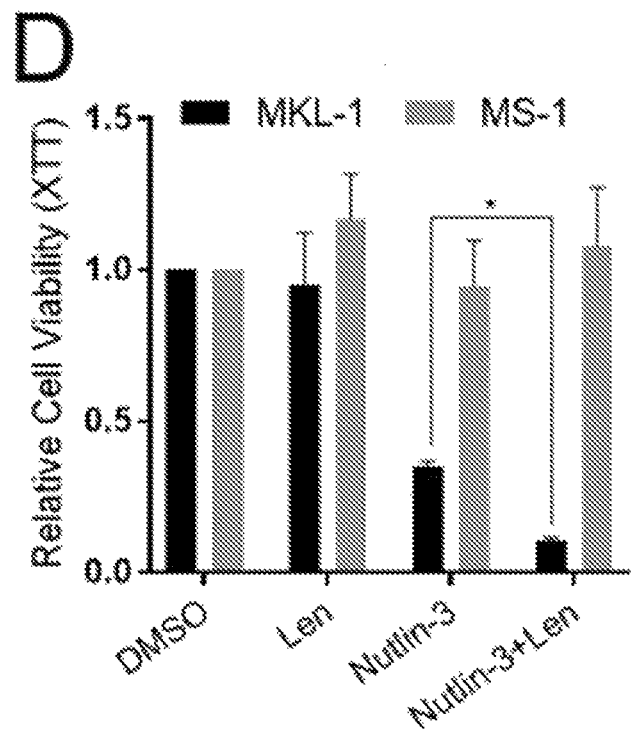
Figure 10E:
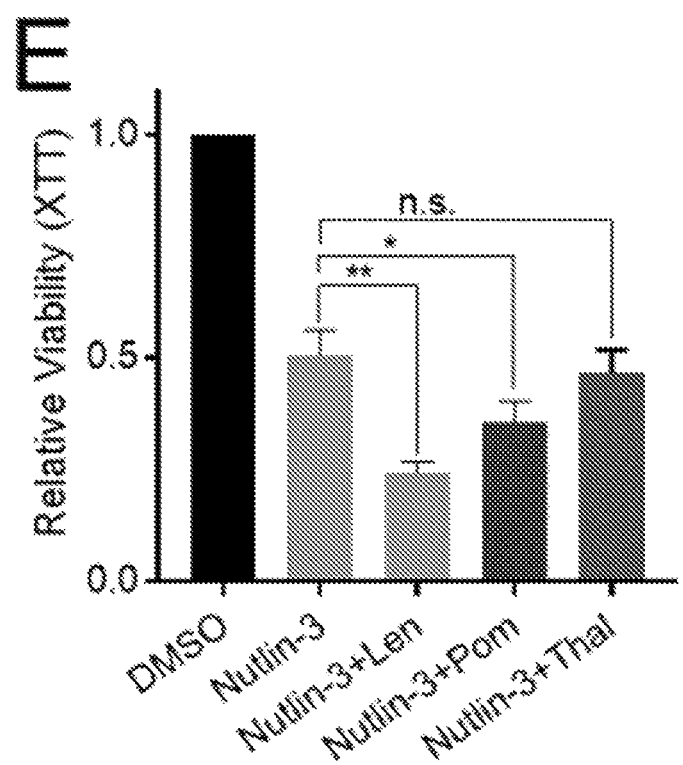
Figure 11A:
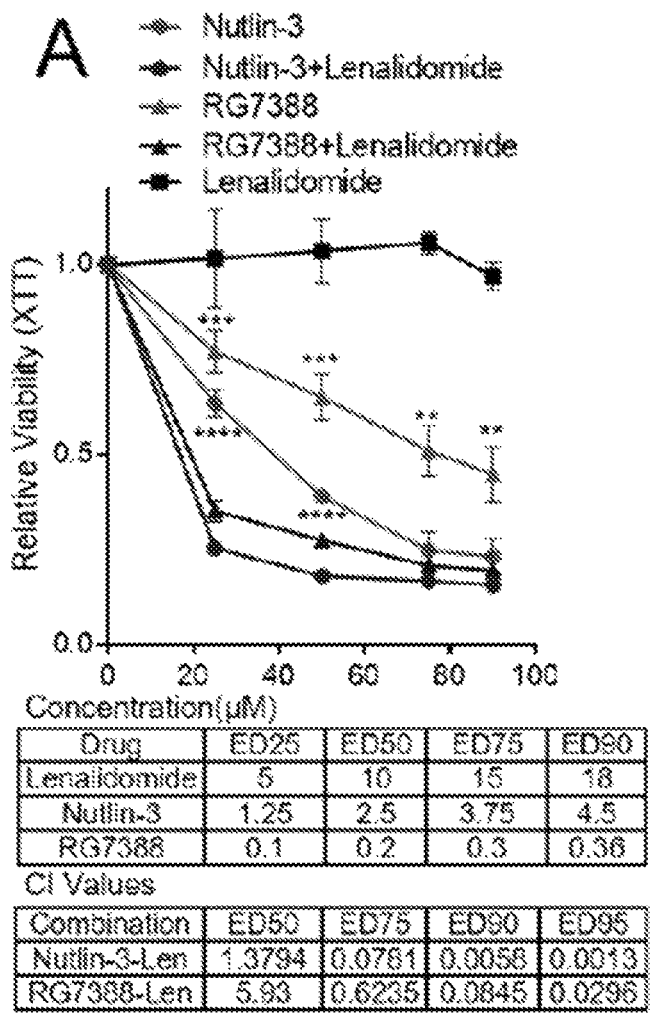
Figure 11B:
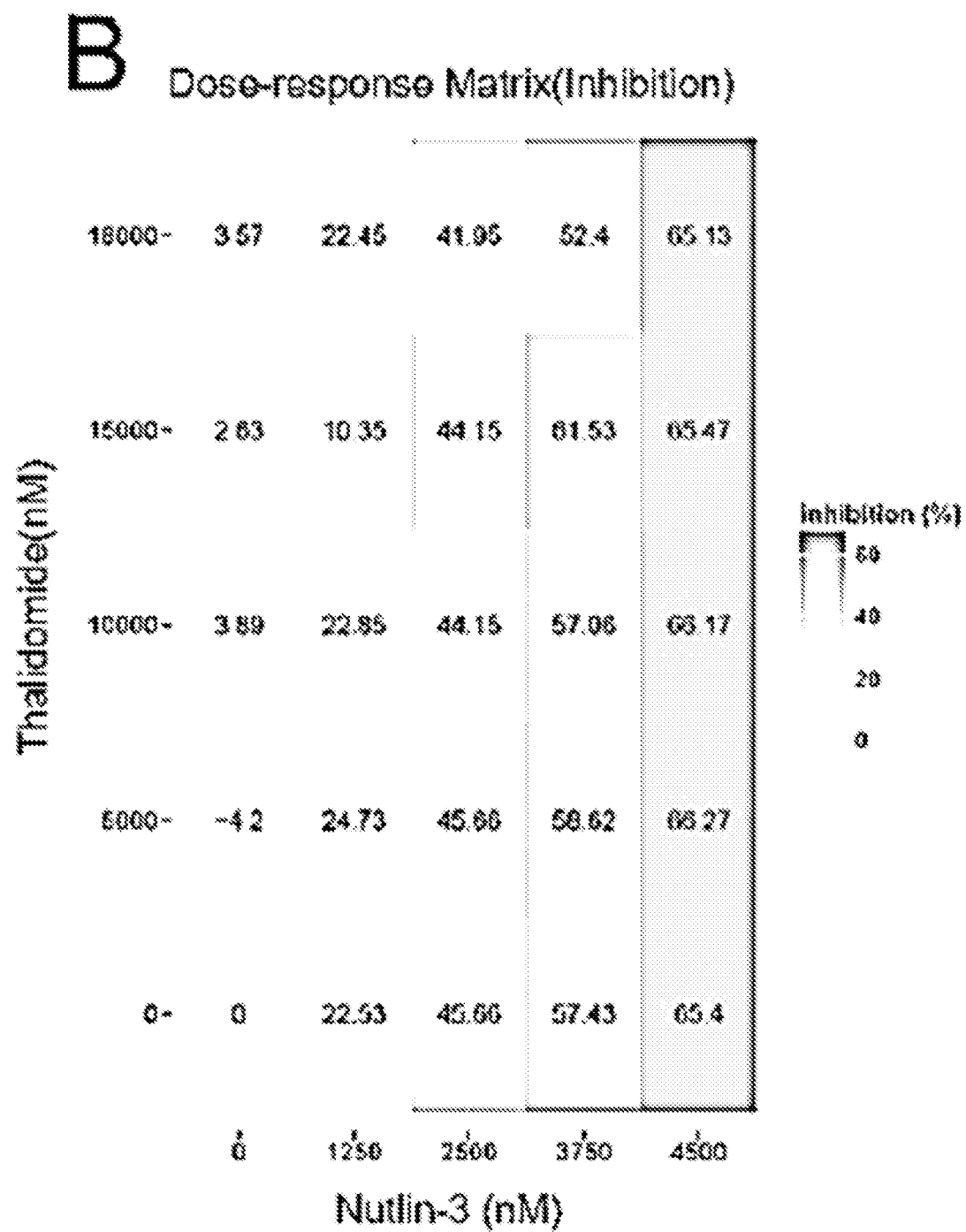
Figure 11C:
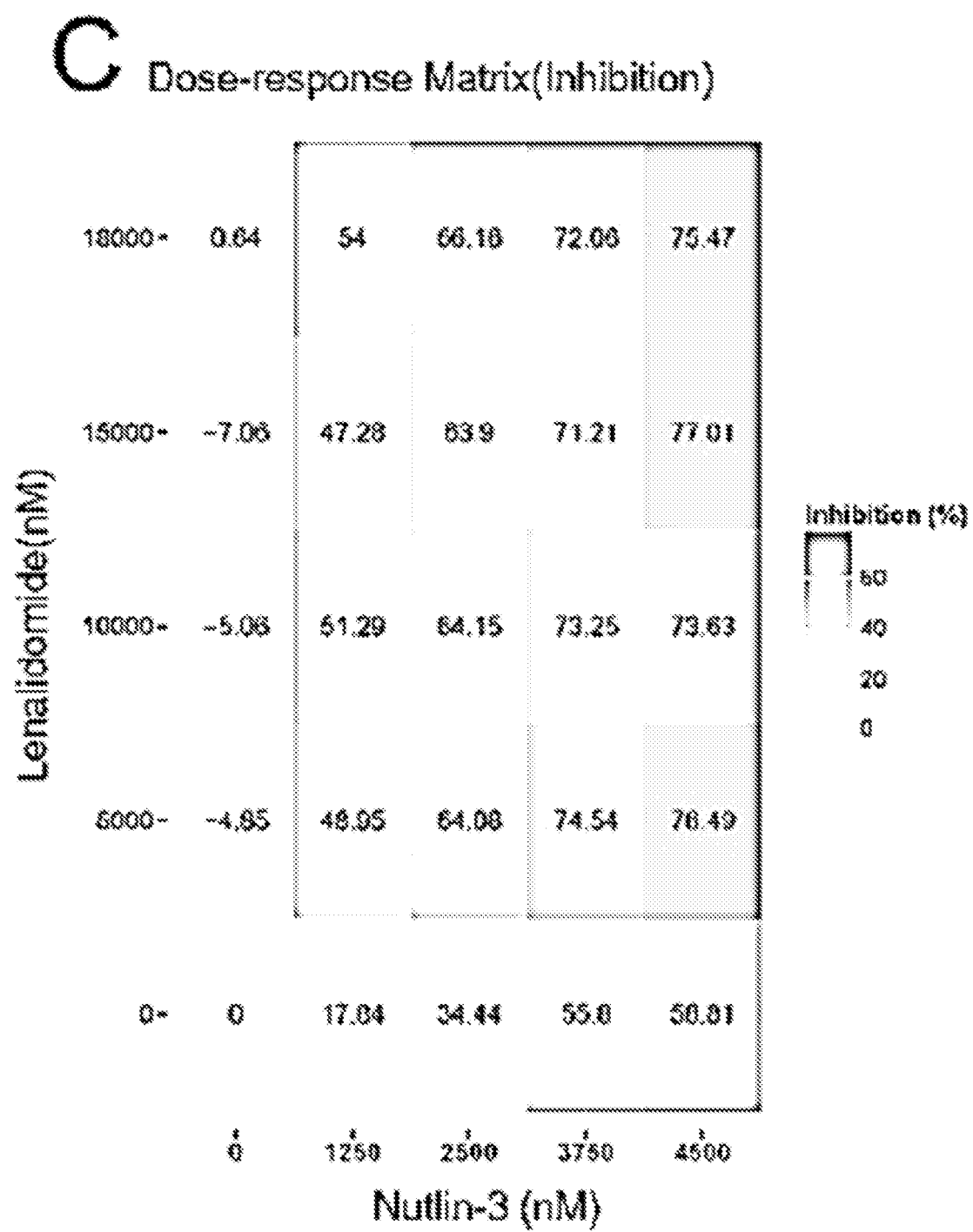
Figure 11D:
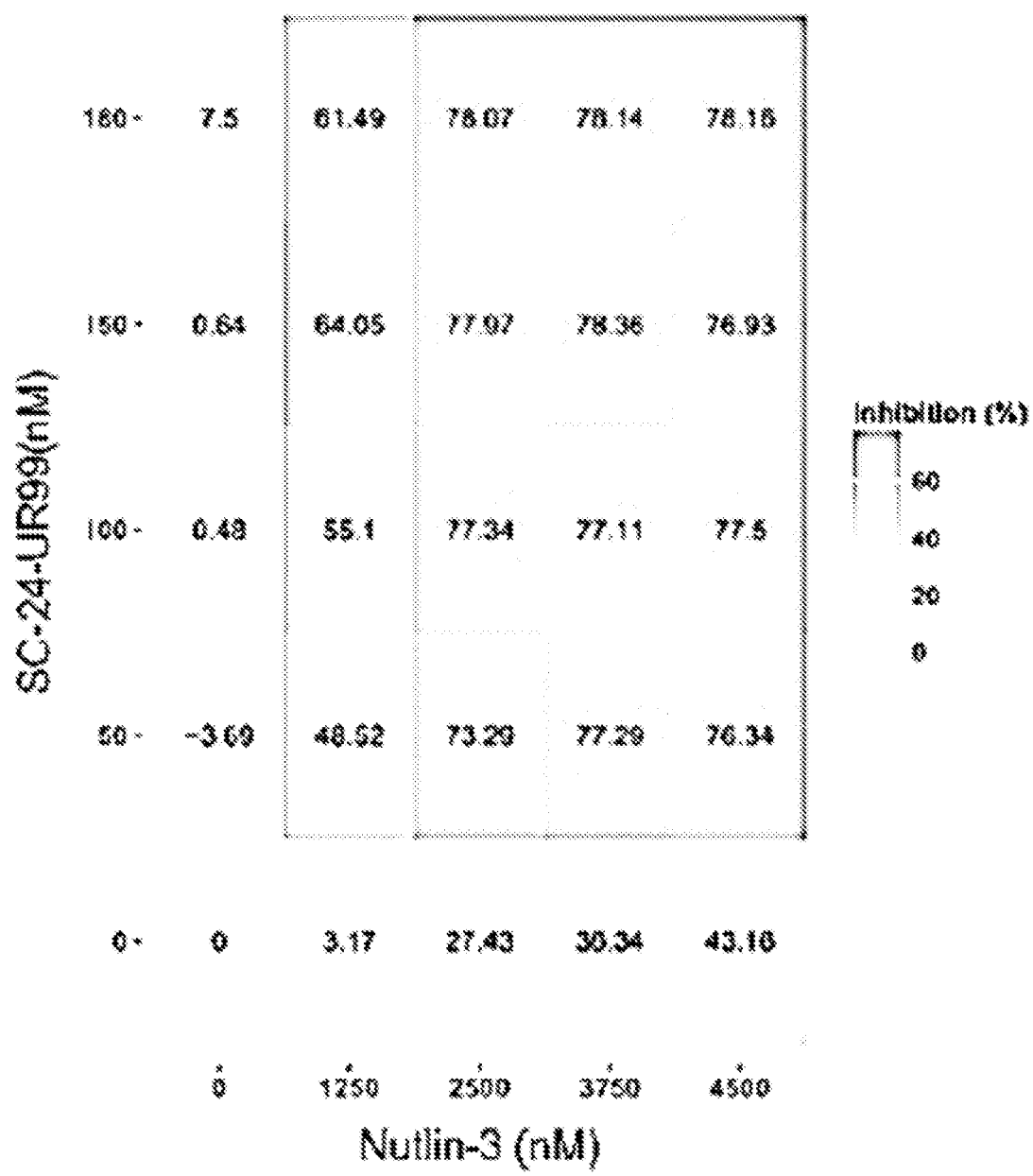
Figure 11E:
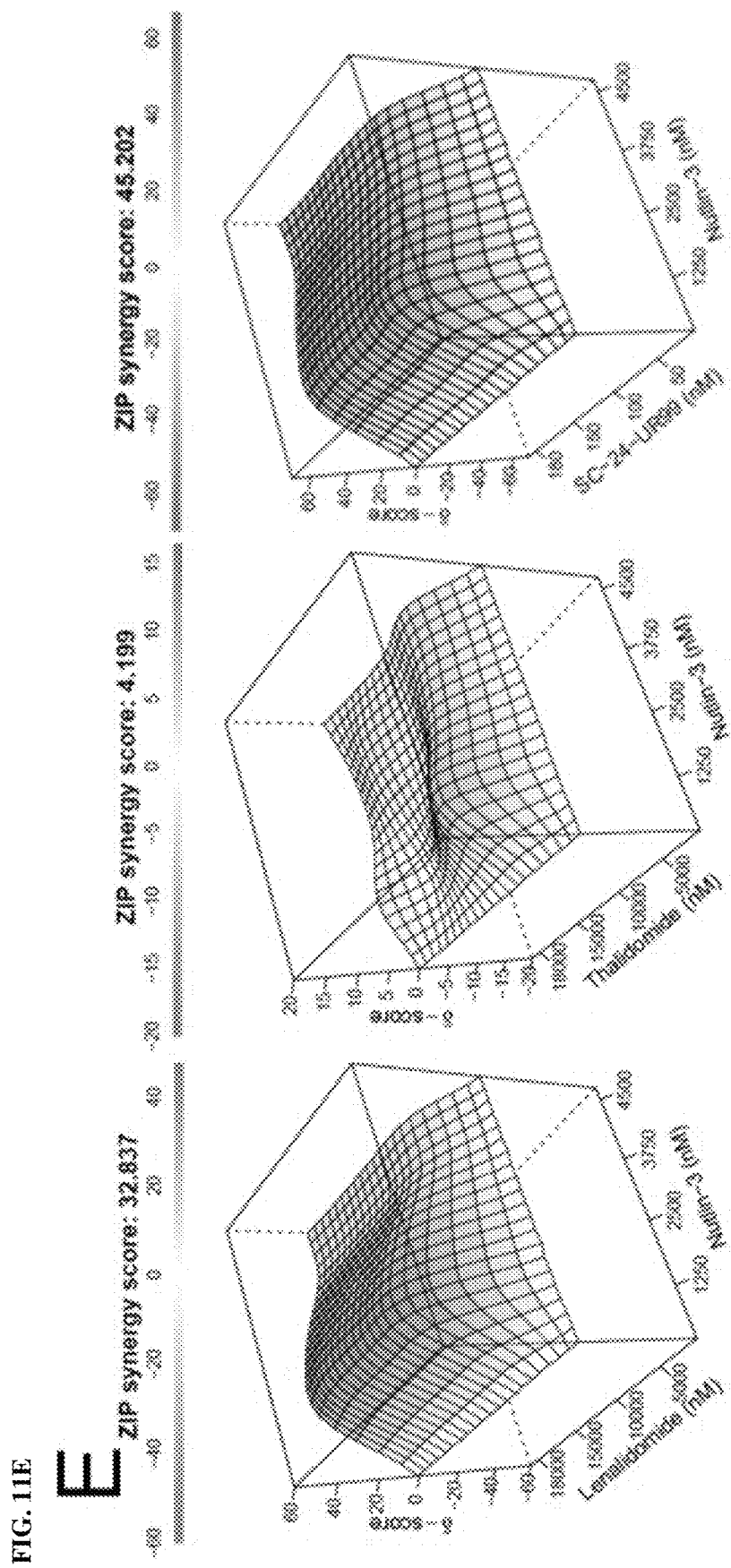
Figure 11F:
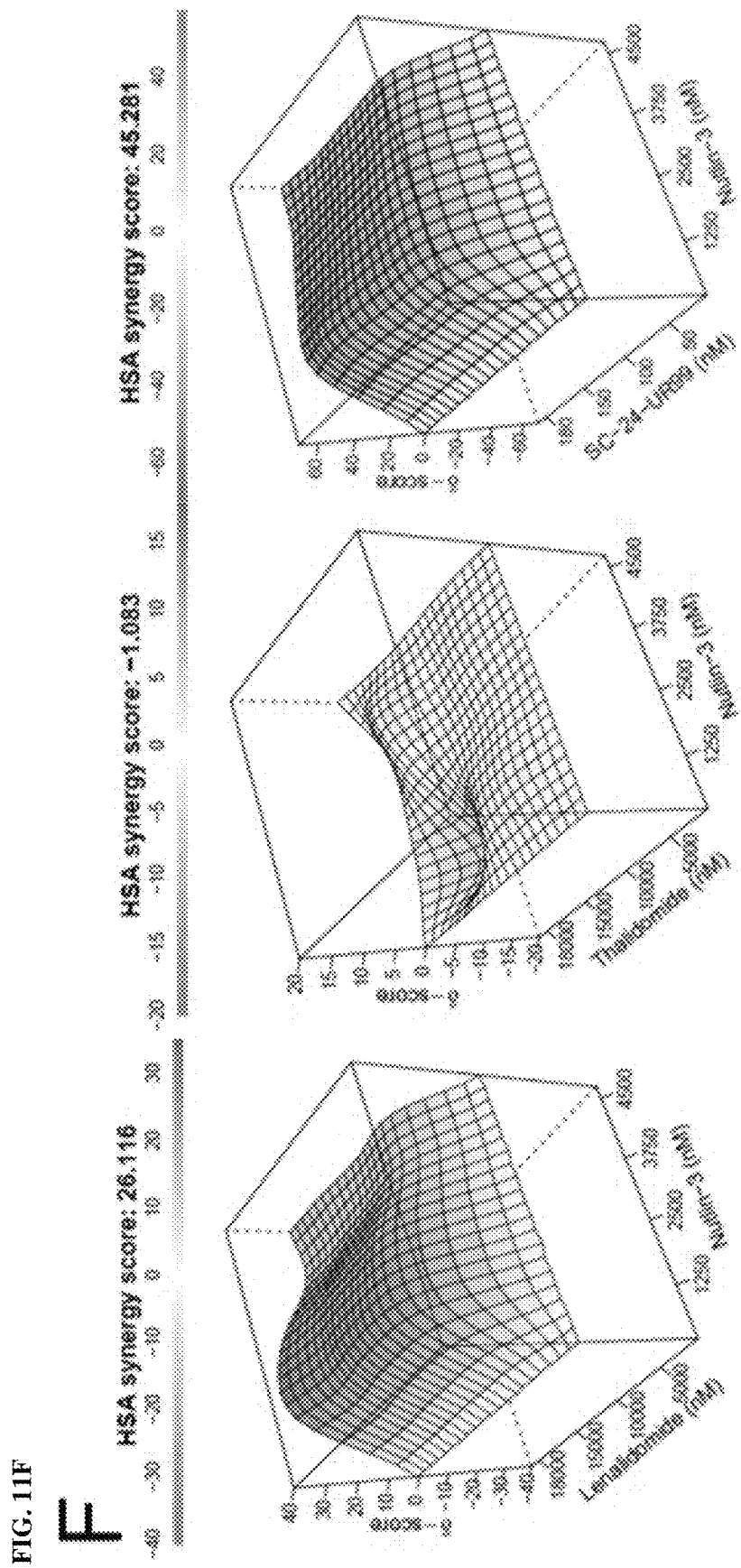

FIG. 8 (herein also referred to as FIG. S3).

A. The ratio of MDM4-FL (Full length) to MDM4-S (short variant).

B. cBioPortal analysis of 101 cases of MCC reveals 37 tumors with TP53 or RB1 mutations and higher levels of mutations compared to MCC (64) without TP53 or RB1 mutations. MDM2 and MDM4 show frequent copy number gains (3-8 copies) and amplifications (>8 copies).

FIG. 9 (herein also referred to as FIG. S4).

A. Lenalidomide reduces CK1α protein rapidly in MKL-1. MKL-1 cells were treated with lenalidomide (Len, 10 µM) and/or cycloheximide (CX, 5 µM) for 2, 4 or 6 hours with or without the MG132 (10 µM). P53 is a positive control for the cycloheximide pulse chase treatment.

B. MKL-1, WaGa, Peta, BroLi and MS-1 MCV-positive MCC cell lines were treated with nutlin-3 (5 µM) with or without lenalidomide (10 µM) for 40 hours.

C. Lenalidomide (10 µM) and pomalidomide (10 µM) to a lesser degree, but not thalidomide (10 µM), decreases CK1α protein levels.

D. MKL-1 cells were treated with nutlin-3, lenalidomide or both for 16 hours followed by cycloheximide treatment for 2 and 4 hours. Western blot bands were quantified using LiCor and normalized to the 0 hour time point for each treatment. p53 half-life is estimated to be 1.5 hours for DMSO and lenalidomide-treated samples and 4 hours for nutlin-3-treated samples. Experiment was performed three times with data shown as mean±SD; **two-way ANOVA<0.005.

E. MKL-1 cells were treated with nutlin-3 (5 µM), lenalidomide (10 µM) or both for 24 or 40 hours and harvested for IP-western blotting with MDM4, p53 and CK1α.

FIG. 10 (herein also referred to as FIG. S5).

A-C. MKL-1 cells were treated with nutlin-3 (A), RG7388 (B), or AMG232 (C) with or without lenalidomide (fixed concentration of 5 µM). XTT was performed at 96 hours treatment.

D. MKL-1 (with wild type p53) and MS-1 (with p53 mutations) were treated with nutlin-3 with or without lenalidomide for 96 days and XTT assay was performed to measure relative cell viability normalized to DMSO controls.

E. Lenalidomide and pomalidomide to a lesser degree, but not thalidomide, synergize with nutlin-3 in reducing MKL-1 viability. The XTT assay was performed at 96 hours of treatment in three biological replicates. Data are shown as mean±SD; *P<0.05, P<0.005, *P<0.0005, ****P<0.00005 and n.s>=0.05.

FIG. 11 (herein also referred to as FIG. S6).

A. Compusyn synergy testing indicates that nutlin-3 and RG7388 synergize with lenalidomide. The XTT assay was performed following treating MKL-1 cells for 96 hours. A CI value less than 1 signifies a synergistic effect.

B-D. Dose-response matrix of nutlin-3 with thalidomide (B), lenalidomide (C) or SC-24-UR99(D).

E. ZIP synergy testing

F. HSA synergy testing.

DETAILED DESCRIPTION OF THE INVENTION

LT Activates and ST Dampens the p53 Response.

To study the effect of MCV T antigens on p53 in normal cells, a doxycycline inducible vector expressing GFP or tumor derived truncated or full-length forms of LT was introduced into IMR90 diploid lung fibroblasts (FIG. 1A, S1A). The truncated forms of LT include L21 (encoding residues 1-292), 162 (residues 1-320) and 168 (residues 1-275) each containing an intact LXCXE motif[6]. LT-L21 or LT-162 expression in IMR90 significantly increased levels of ARF and several p53 target genes including GDF15 and p21 (CDKN1A) as assessed by RT-qPCR (FIG. 1A). Inhibition of RB activates the E2F transcription factors leading to increased levels of ARF[10]. ARF is a potent inhibitor of the major p53 degrading E3 ligase MDM2[14]. LT expression increased protein levels of p53 as well as phospho-Serine 15 p53 (P-p53) and p21 indicative of p53 activation (S1A). Expression of LT-162 also led to increased levels of cleaved PARP (**), indicating an apoptotic response.

Figure 1B:
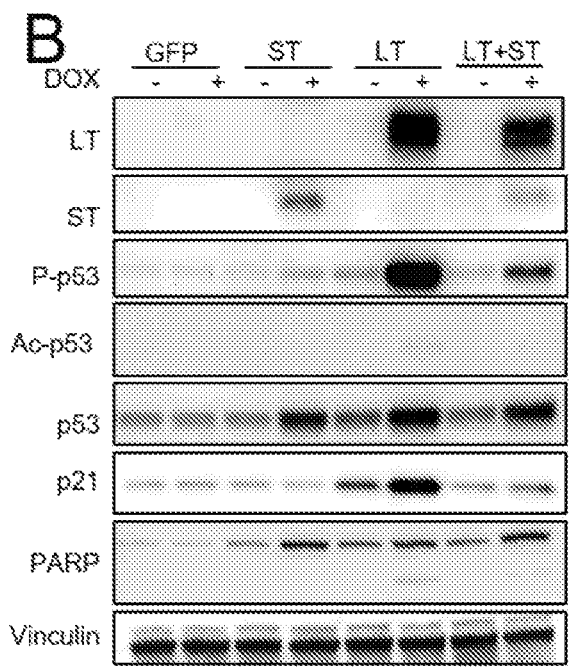
Figure 1C:
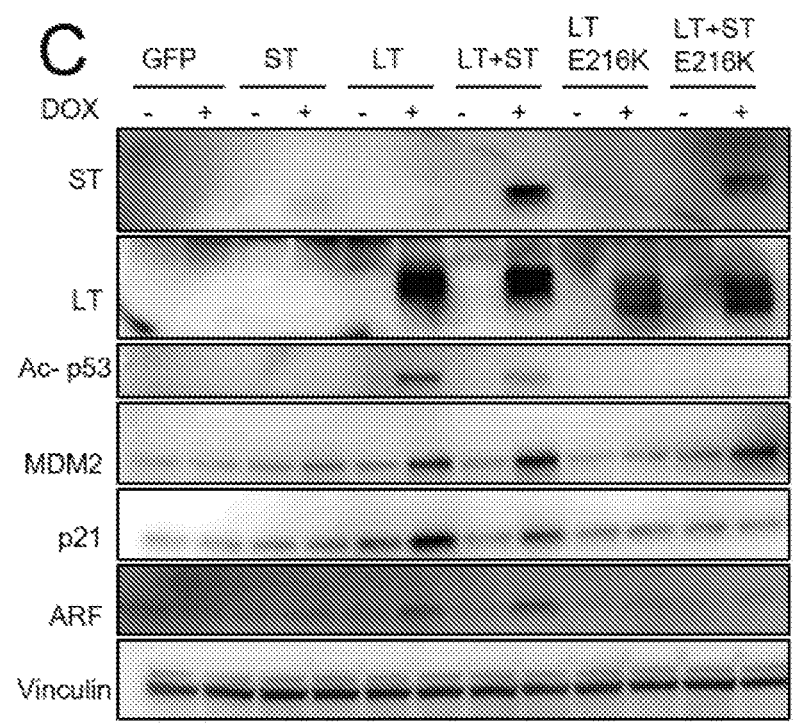

LT and ST are co-expressed as splice variants from the integrated MCPy V viral DNA in MCC tumors. To mimic this in IMR90 cell lines, the present inventors introduced a genomic version of LT-L21 that co-expresses ST. When ST was co-expressed with LT-L21, lower levels of p53 activation (p21, p-p53 and acetyl-Lysine 382 or Ac-p53) were observed compared to the response to LT-L21 only (FIG. 1B, S1B). The results indicate that truncated LT can activate p53 while ST can reduce this response when coexpressed. To determine if increased levels of ARF required LT binding to RB, the present inventors introduced a point substitution mutation in the LXCXE motif (E216K) of LT-L21. When stably expressed in HCT116 cells, L21-E216K was unable to co-precipitate RB but retained binding to VPS39 that binds to a different region of LT (S1C)[5]. When expressed in IMR90 cells, L21-E216K did not increase levels of ARF, p21, p53 or Ac-p53 (FIG. 1C). These results indicate that LT binding to RB contributes to increased levels of ARF and activation of the p53 response. Of note, increased levels of MDM2 but not p21 were detected when ST was co-expressed with L21-E216K.

MDM2 and CK1α are Transcriptional Targets of the ST-MYCL-EP400 Complex.

Figure 2A:
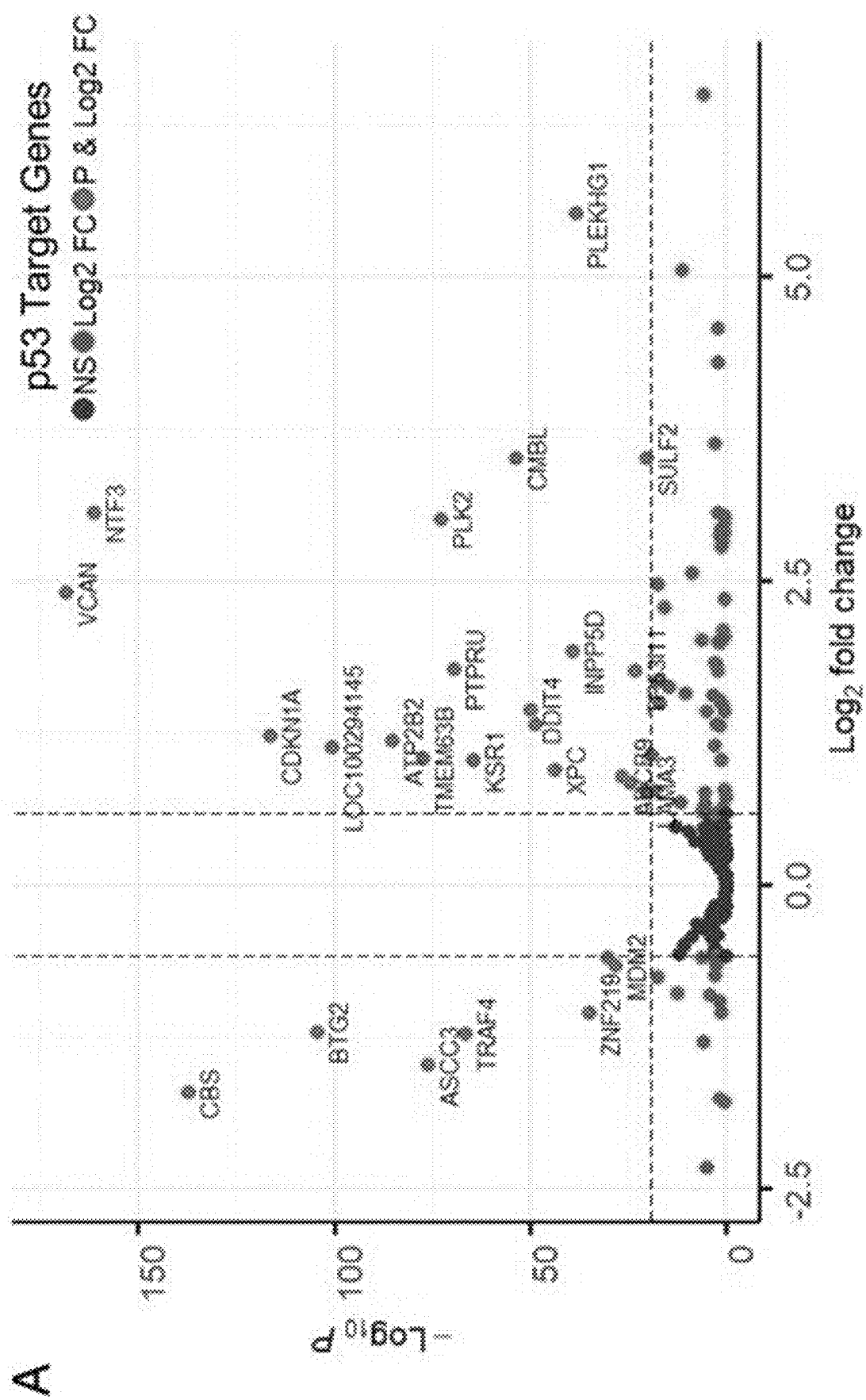
Figure 2B:
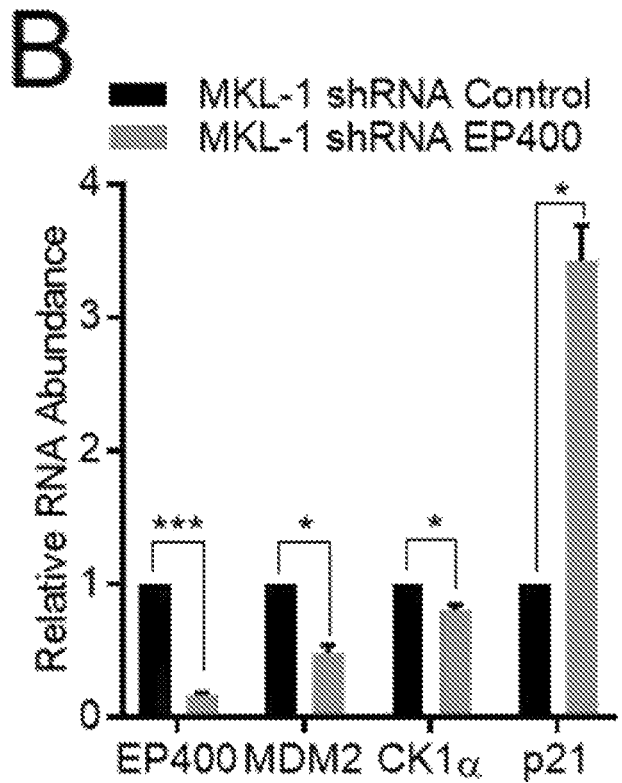

The present inventors recently reported that MCV ST recruits the MYC homologue MYCL (L-Myc) to the EP400 chromatin remodeler complex to bind specific gene promoters and activate their expression[15]. To identify genes regulated by the ST-MYCL-EP400 complex in MKL-1 cells, RNA-seq was performed after depleting EP400 using three different shRNAs[15]. Using the reported RNA-seq results, the present inventors assessed changes in gene expression of known p53 target genes[9]. EP400 depletion led to increased levels of many p53 target genes including p21 (CDKN1A), as visualized by a volcano plot (FIG. 2A). Using the fold change cutoff of 1.5, 59 genes were upregulated and 17 downregulated of 198 total p53 target genes (Table S1)[9]. EP400 depletion also led to a decrease in MDM2 E3 ligase and CK1α levels (FIG. 2B, S2A-C). MDM2 and MDM4 contain an N-terminal p53-binding domain that binds directly to the transactivation domain of p53 to block p53 activation[11]. MDM4 can regulate its own activity toward p53. The N-terminal p53-binding domain of MDM4 forms an intra-molecular interaction with its central W motif region and thereby reduces binding to p53[12]. CK1α (CSNK1A) is a serine/threonine kinase that binds and phosphorylates MDM4, which in turn prevents this auto-inhibitory interaction and activates MDM4[13]. RT-qPCR and western blotting confirmed that p21 levels increased and MDM2 and CK1α levels decreased upon EP400 knockdown in MKL-1 cells (FIG. 2B, S1C).

Figure 2C:
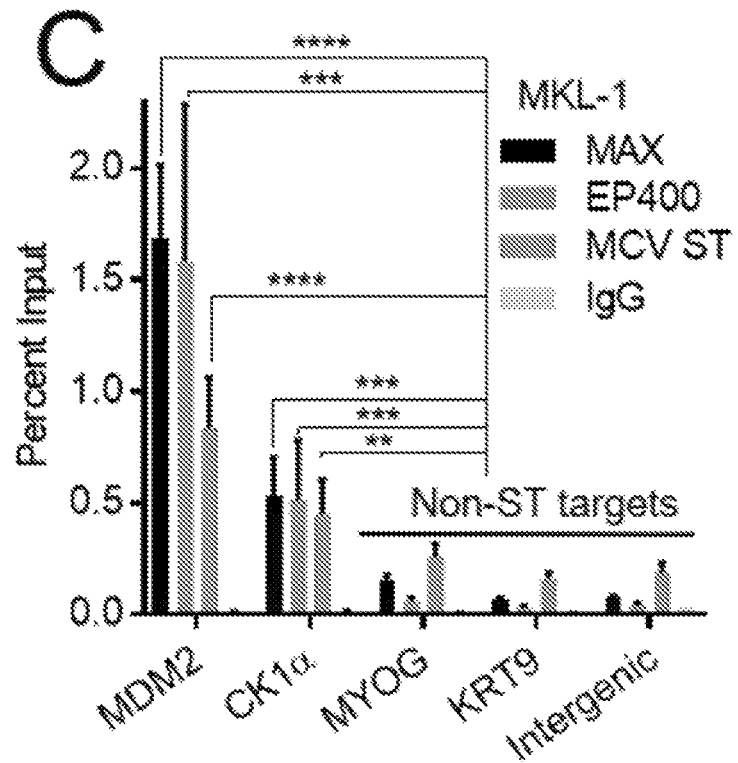
Figure 2D:
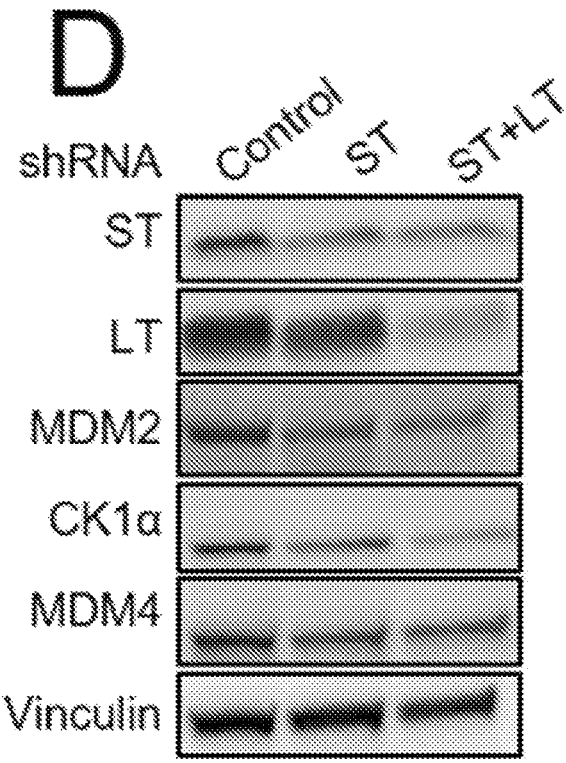

ChIP-seq with antibodies to ST, MAX (which dimerizes with MYCL) and EP400 revealed enrichment for the MDM2 and CK1α promoters (S2E)[15]. The present inventors performed ChIP-qPCR for MAX, ST and EP400 and observed specific enrichment for these promoter (FIG. 2C). The present inventors depleted ST or ST and LT using specific shRNAs in MKL-1 cells and found that the levels of MDM2 and CK1α decreased expression of the shRNAs (FIG. 2D)[16]. This result together with the RT-qPCR and ChIP data indicates that MDM2 and CK1α are direct transcriptional targets of the ST-MYCL-EP400 complex. Of note, MDM4 levels decreased upon depletion of ST, although the present inventors did not find evidence for direct activation of MDM4 by ST. ST increases levels of CK1α that could serve to activate MDM4 activity towards p53.

Figure 2E:
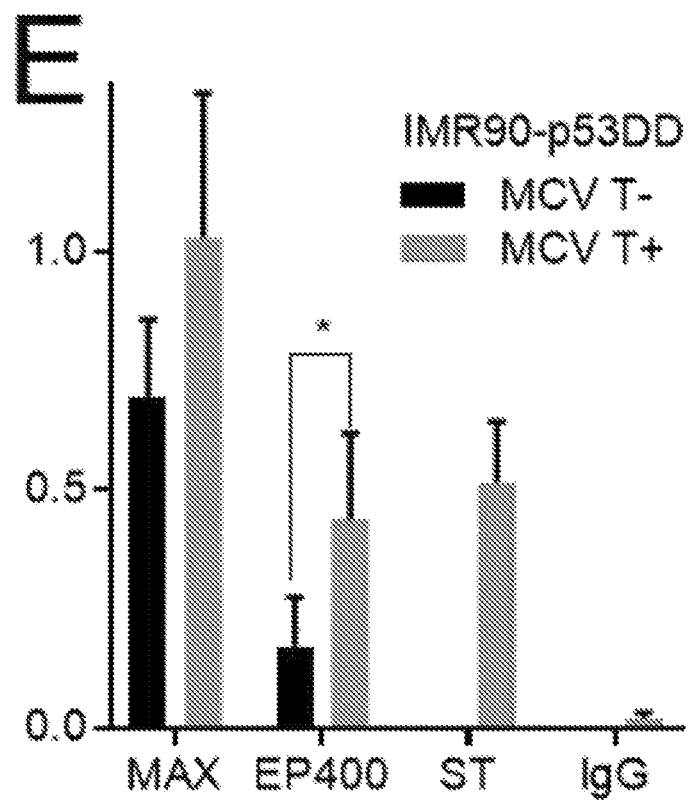
Figure 2F:
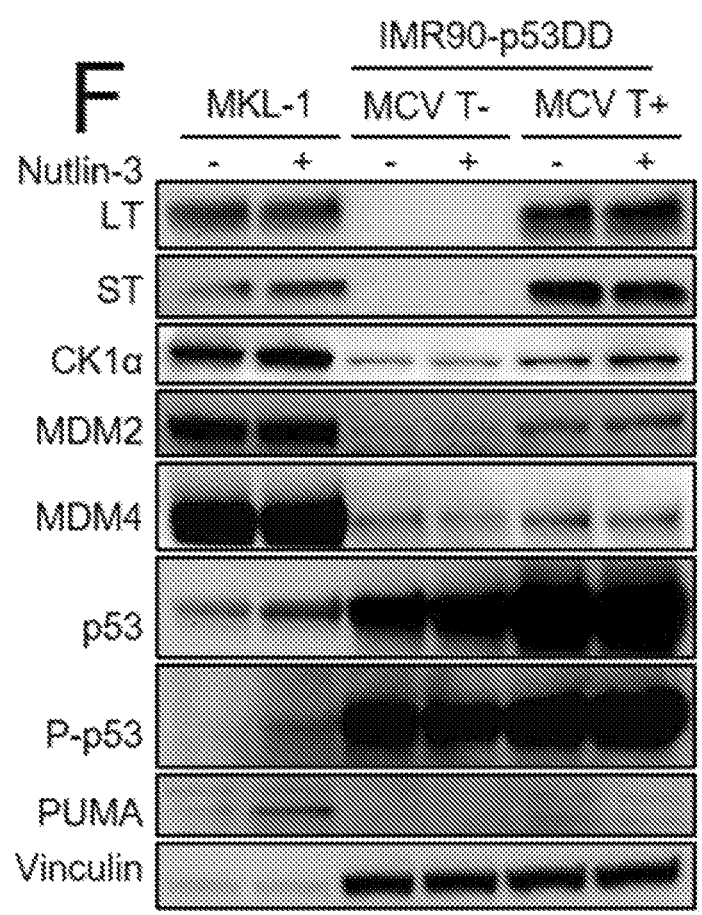

Since MDM2 is a p53 target gene, it is possible that the MCV T antigens indirectly increase MDM2 levels by activating p53[9]. To exclude this possibility, the present inventors introduced a dominant-negative version of p53 (p53DD) that binds and inactivates the endogenous p53 into IMR90 cells[17]. The IMR90-p53DD cells were further transduced with MYCL and MCV LT-L21 with ST[17]. The present inventors detected ST binding to the MDM2 and CK1α promoters by ChIP-qPCR and observed that EP400 enrichment to the MDM2 promoter increased in the presence of MCV T antigens (FIG. 2E, S2F). MDM2 inhibitor treatment with nutlin-3 did not increase p53, p-p53 and PUMA levels, indicative of p53 activation (FIG. 2F, S1D). To further determine the ST-MYCL-EP400 complex binds to these promoters independently of p53, the present inventors depleted p53 in MKL-1 with shRNA and performed ChIP-qPCR of EP400 and ST (S2G). The present inventors found that p53 did not affect EP400 and ST enrichment to the MDM2 and CK1α promoters. These results indicate that MCV ST transactivates MDM2 and CK1α in MCC and IMR90 cells, independently of p53.

MDM4 is Overexpressed in Virus-Positive MCC.

Figure 3A:
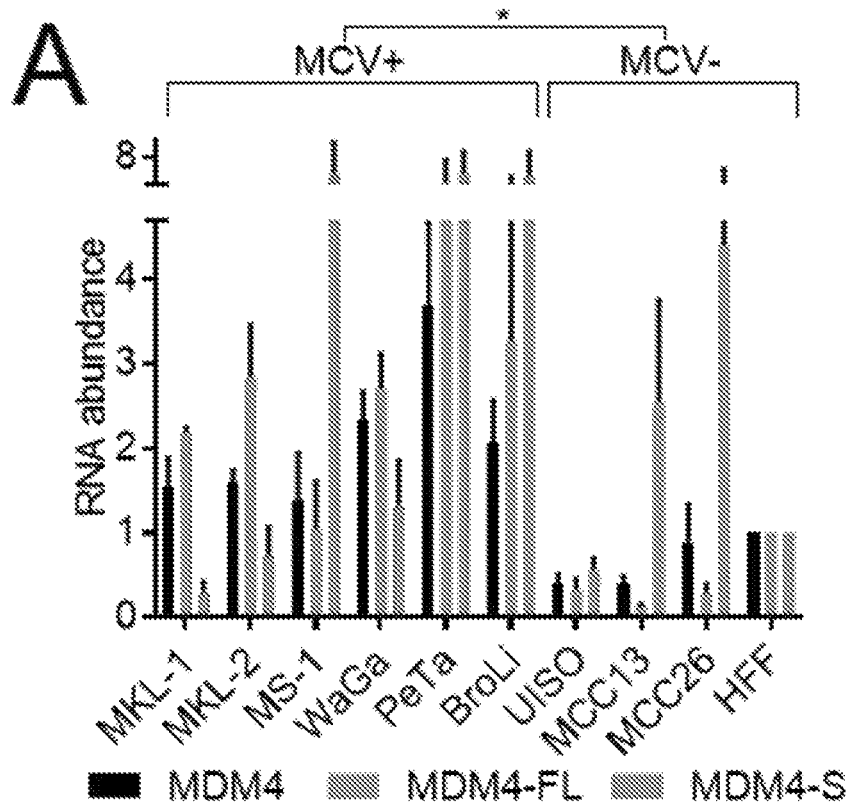
Figure 3B:
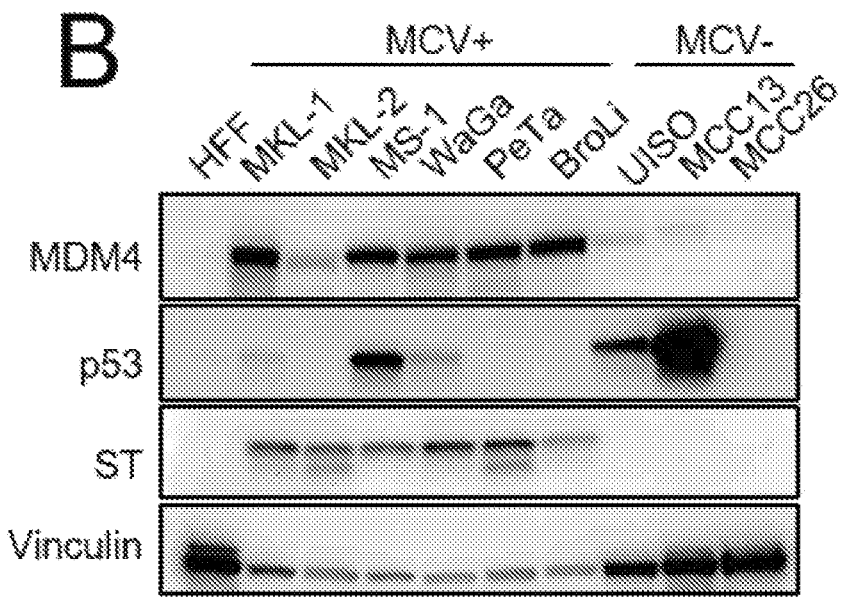

Overexpression of MDM4 can be found in some cancers with wild type p53[18]. The present inventors used three sets of MDM4 primers to assess total MDM4 (all splice variants), MDM4-FL (Full length) and MDM4-S (short variant missing the RING domain) levels in MCC cell lines[18]. Virus-positive (MKL-1, MKL-2, MS-1, WaGa, PeTa, and BroLi) MCC cell lines had significantly higher levels of total MDM4 and MDM4-FL relative to the virus-negative (UISO, MCC13, and MCC26) MCC lines (FIG. 3A). Furthermore, the MDM4-FL to MDM4-S ratio was higher in virus-positive lines (S3A). The present inventors assessed MDM4-FL protein levels in these MCC cell lines. Virus-positive MCC cell lines expressed high levels of MDM4-FL compared to virus-negative MCC cells lines (FIG. 3B). Of note, the virus-negative UISO cell line had a high MDM4-FL to MDM4-S ratio but did not express abundant levels of MDM4 protein (FIG. 3A, S3A). LT's activation of p53 in virus positive MCC may create dependency on MDM2 and MDM4 expression. Targeted next-generation sequencing (Oncopanel) of 101 MCC tumors revealed frequent low copy gains (3-8 copies) of MDM4 regardless of the presence of MCV (S3B)[19].

Inhibition of MDM2 and MDM4 Activates p53 in MCC.

The present inventors observed that nutlin-3 MDM2 inhibitor treatment activated p53 as shown by increased levels of total p53, P-p53, Ac-p53, p21 and PUMA in MKL-1, WaGa, PeTa and BroLi MCC cell lines containing wild type p53, but not in MS-1 cells harboring an inactivating p53 mutation (FIG. 2F, FIG. 4A, 52B)[20]. Recent reports demonstrated that the CRBN (Cereblon) E3 ligase can specifically target CK1α for ubiquitination in the presence of lenalidomide [21, 22]. The present inventors assessed whether lenalidomide could decrease CK1α levels and activate p53 in MCC cells. MKL-1 cells were treated with lenalidomide with or without cycloheximide to block protein synthesis. Although CK1α levels did not change appreciably with cycloheximide treatment for 6 hours, levels rapidly decreased following addition of lenalidomide (S4A).

Figure 4A:
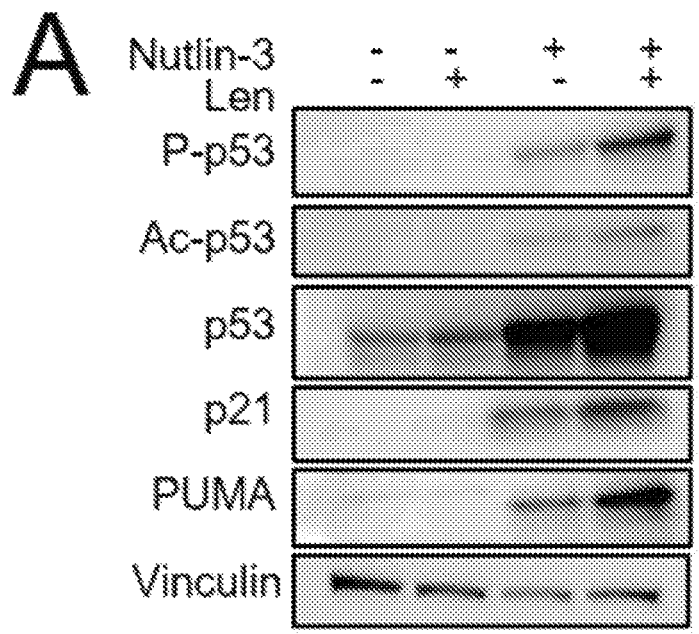
Figure 4B:
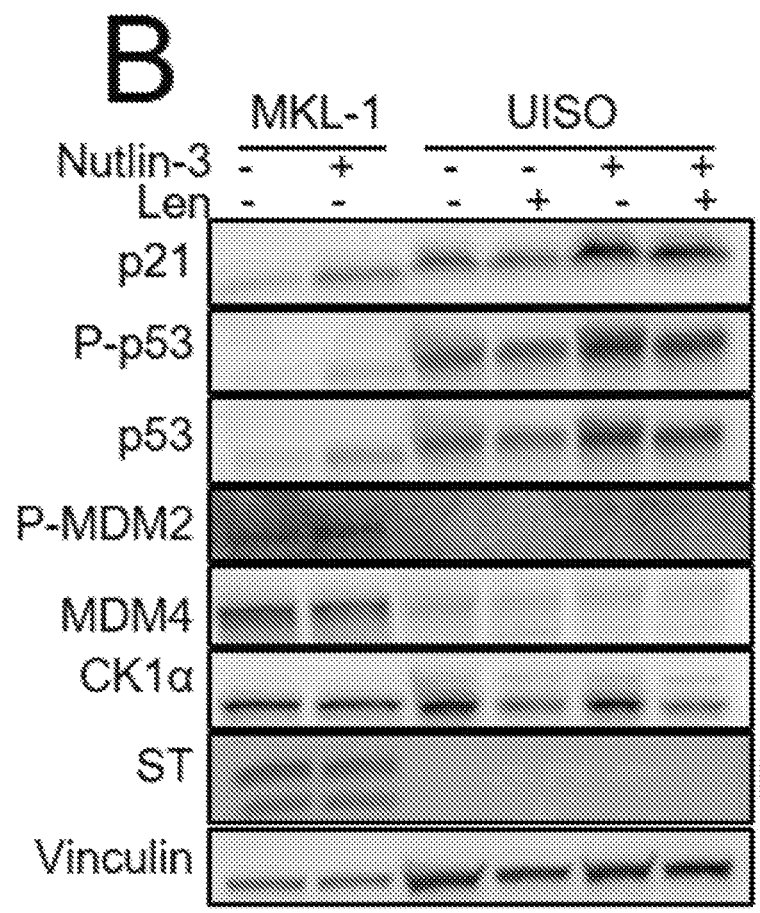

Lenalidomide treatment alone had a modest positive effect on p53 levels. However, when nutlin-3 and lenalidomide were combined, larger increases in p53 and p53 target genes were observed in the cell lines with wild type p53 (FIG. 4A, S4B). The present inventors assessed p53 stability (FIG. 4A, S4B). The present inventors assessed p53 stability in MKL-1 cells treated with nutlin-3, lenalidomide or both in the presence of cycloheximide by quantitative western blotting (S4D). Lenalidomide significantly increased the stability of p53 in the presence of nutlin-3[23]. Depletion of CK1α by lenalidomide may decrease MDM4's activities towards p53. The present inventors tested whether lenalidomide enhances p53 activation in virus-negative and p53-wildtype UISO cells which express little MDM2 and MDM4 (FIG. 3A-B). The present inventors observed that lenalidomide decreased the CK1α levels but failed to enhance p53 activation by nutlin-3 in UISO cells (FIG. 4B).

Figure 4C:
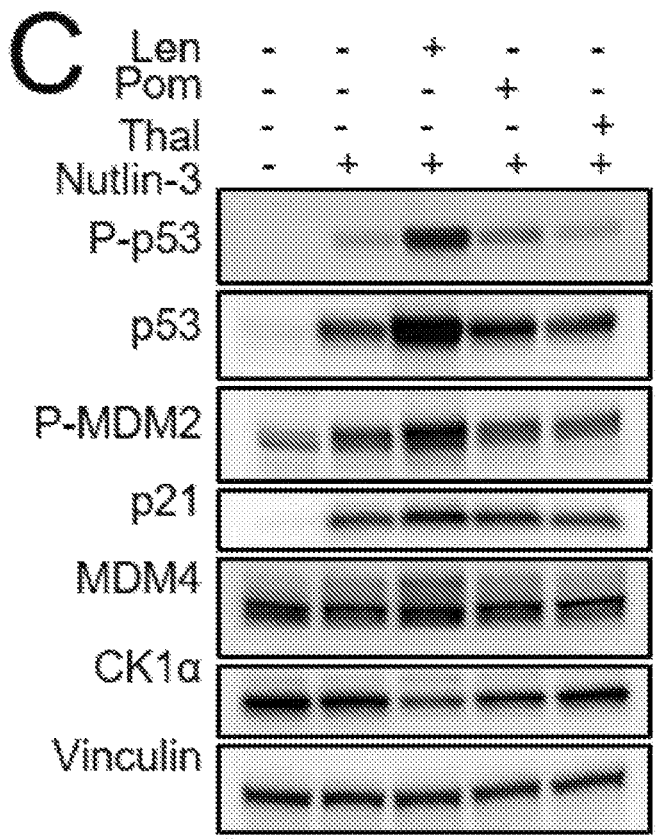
Figure 4D:
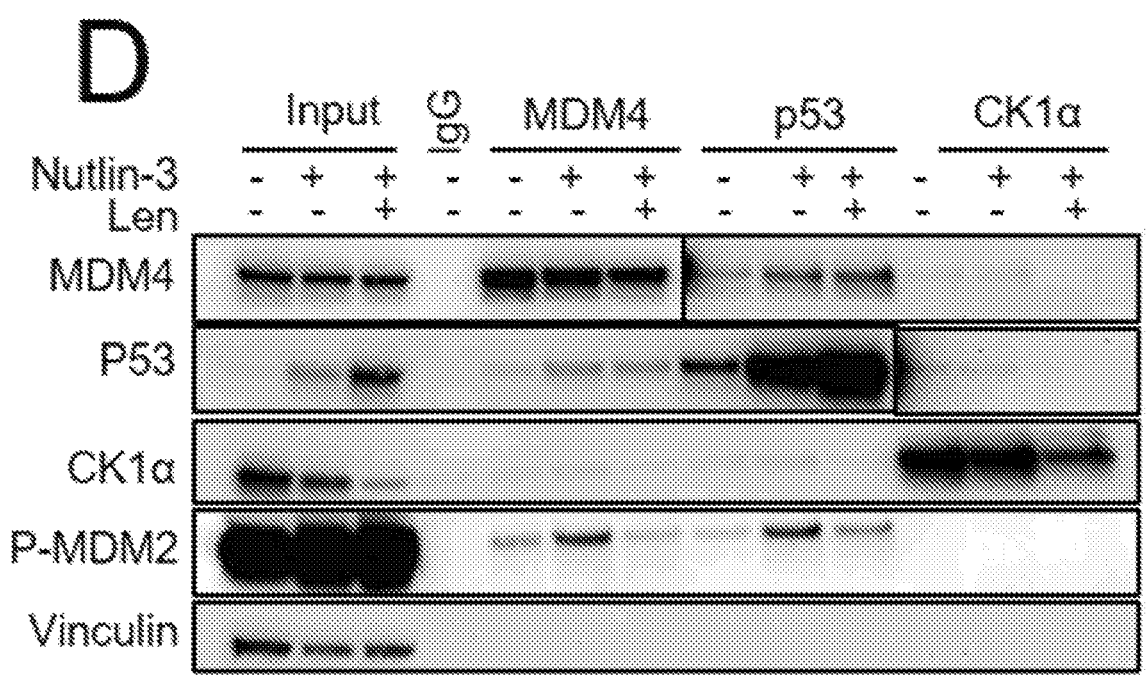
Figure 4E:
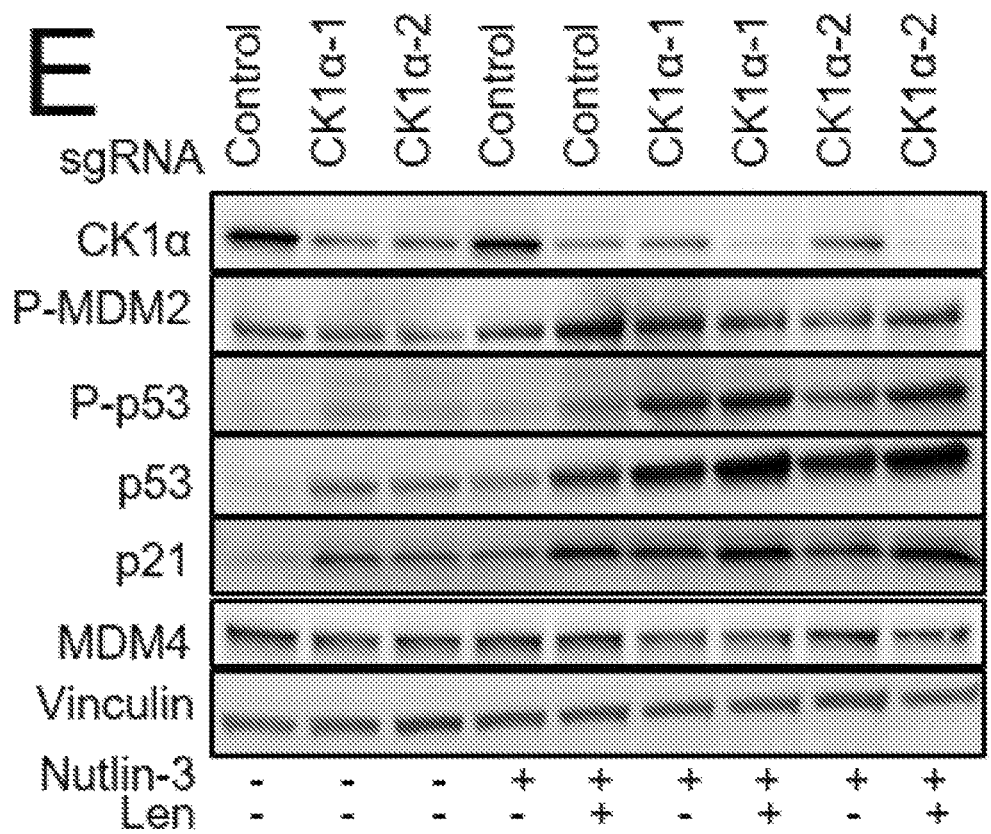
Figure 4F:
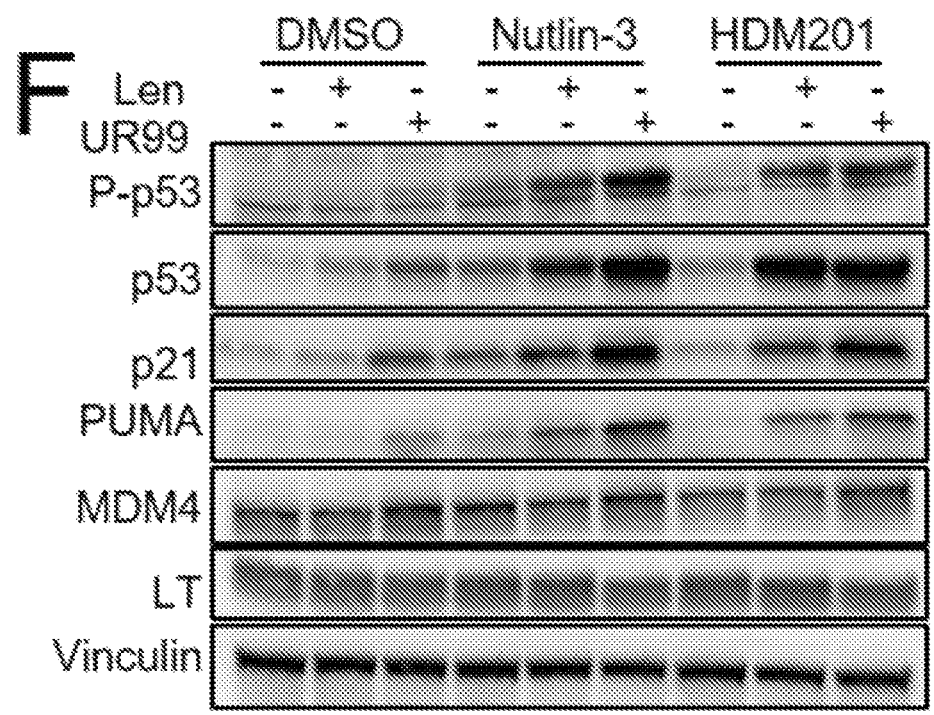

Structural analysis of CRBN revealed that lenalidomide could strongly promote the interaction with CK1α while the related compounds thalidomide and pomalidomide were much less capable of recruiting CK1α to CRBN[22]. Compared to lenalidomide, pomalidomide and thalidomide did not reduce CK1α protein levels in MKL-1 cells (S4C). Furthermore, pomalidomide or thalidomide did not enhance the p53 response to nutlin-3 in MKL-1 cells (FIG. 4C). To test the contribution of CK1α to MDM4 binding to p53, the present inventors performed immunoprecipitation (IP) for MDM4, p53 and CK1α with lysates prepared from MKL-1 cells treated with nutlin-3 and lenalidomide for 40 hours (FIGS. 4D and S4E). Lenalidomide and nutlin-3 reduced CK1α levels and increased p53 levels relative to nutlin-3 only. Despite the increased levels of p53, lenalidomide co-treatment with nutlin-3 did not increase coprecipitation of p53 by MDM4, CK1α or activated MDM2 compared to untreated or nutlin-3 treated controls. This indicates that reduced levels of CK1α decreased MDM4 binding to p53.

If CK1α enables MDM4 binding to p53, the present inventors expected that loss of CK1α would reduce MDM4 binding to p53 and enhance p53 activation[13]. To test this, the present inventors depleted CK1α in MKL-1 by two independent CRISPR sgRNAs and assessed p53 activation following nutlin-3 treatment (FIG. 4E)[24]. CRISPR knockout of CK1α led to increased p53 activity assessed by increased levels of activated MDM2 (phospho-Serine 166, P-MDM2), P-p53, p53 and p21, indicating that a reduction of CK1α either by lenalidomide or sgRNAs, enhances p53 activation[25]. Notably, addition of lenalidomide reduced CK1α protein that was not completely depleted by CRISPR and further increased the marks of p53 activation. The present inventors tested whether a newly developed MDM4 inhibitor (SC-24-UR99, UR99) can enhance the activities of MDM2 inhibitors nutlin-3 or HDM201 (FIG. 4F)[26]. UR99 specifically blocks MDM4 binding to p53. The present inventors found that inhibition of MDM4 by UR99 increased p53 activation by the MDM2 inhibitors.

Lenalidomide Synergizes with MDM2 Inhibitors to Induce Apoptosis in MCC Cell Lines.

Figure 5A:
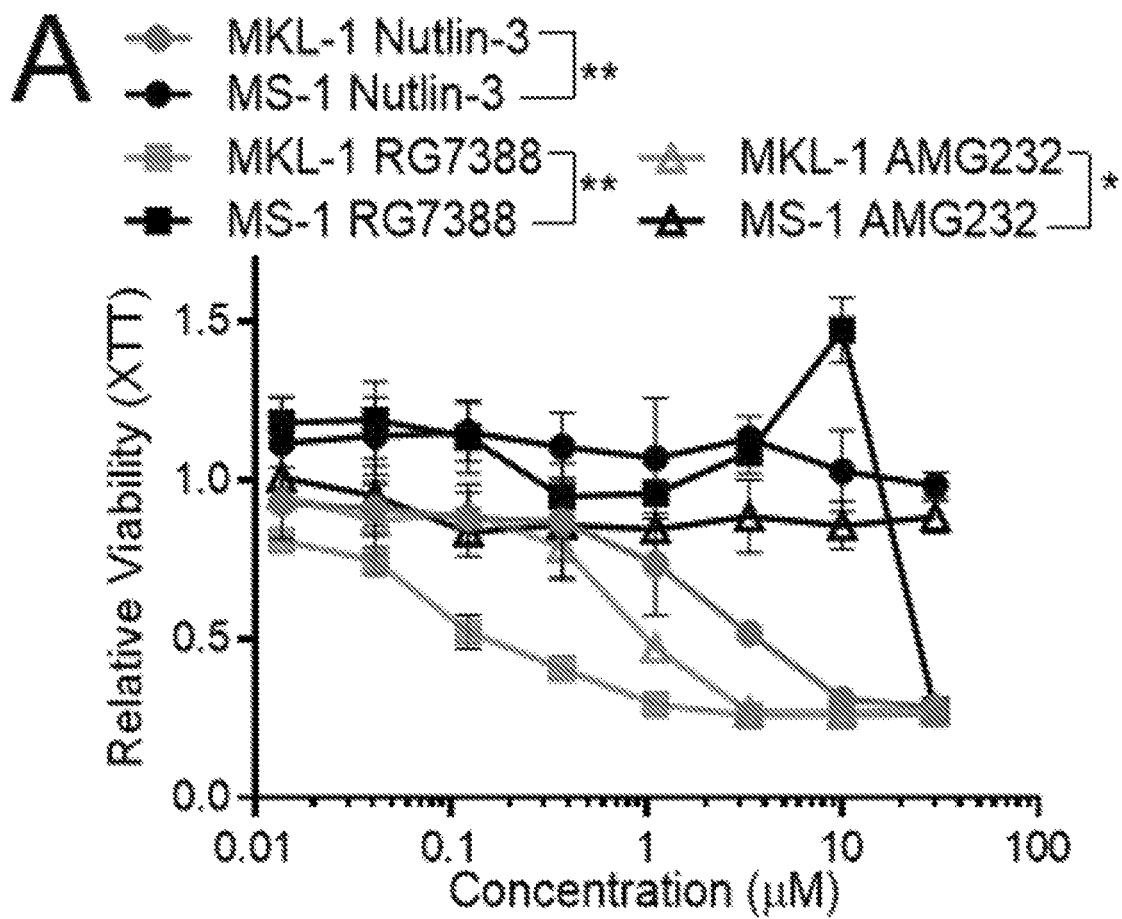
Figure 5B:
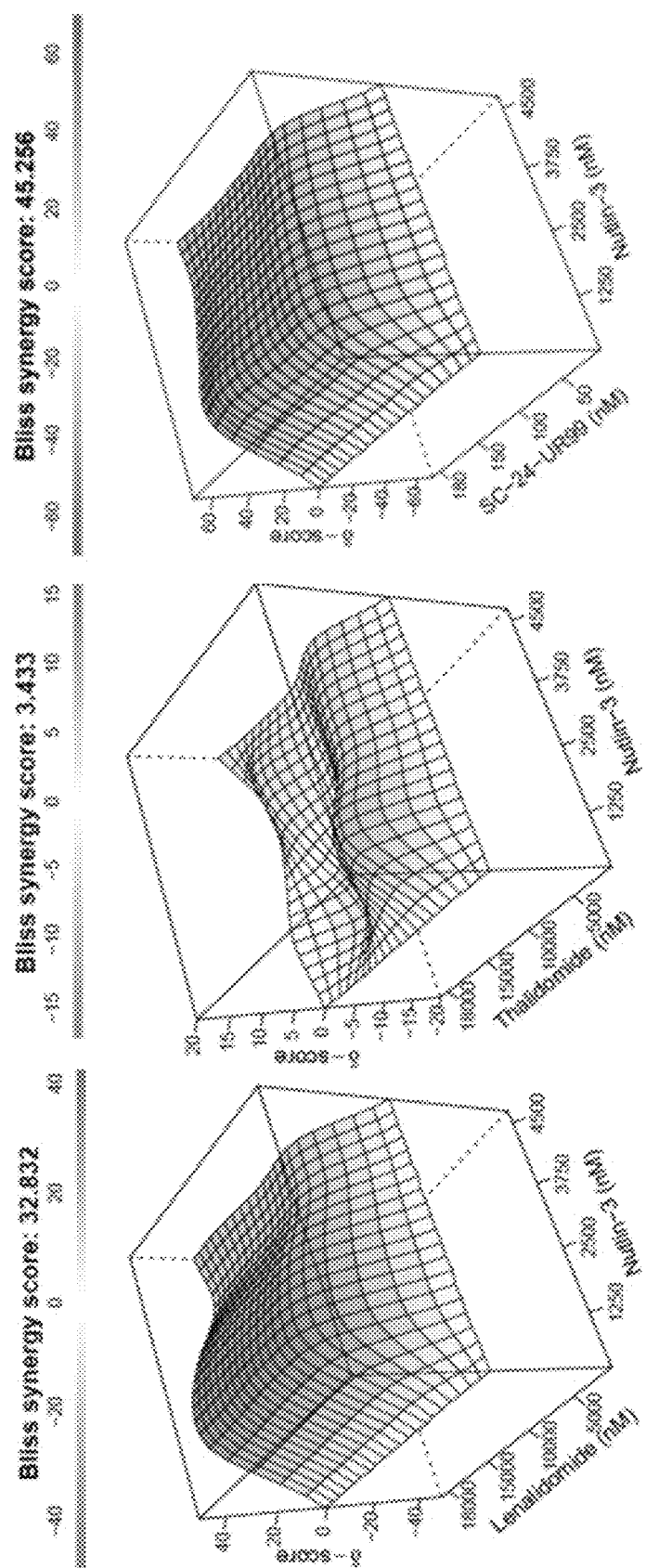

To probe the effect of MDM2 inhibition on MCC cell viability, the present inventors treated MKL-1 (p53 wild type) and MS-1 (p53 mutant) cells with the MDM2 inhibitors nutlin-3, RG7388 or AMG232 for 96 hours and performed an XTT viability assay [27]. MKL-1 but not MS-1 cells were sensitive to all three MDM2 inhibitors (FIG. 5A). The present inventors tested the effect of combining lenalidomide with nutlin-3, RG7388 and AMG232 and observed significantly improved cytotoxicity of all three MDM2 inhibitors when used with lenalidomide (S5A-D). Synergy testing using the Compusyn (S6A) and Bliss (FIG. 5B) methodologies revealed synergistic activity for the combination of nutlin-3 or RG7388 with lenalidomide or UR99 (S6B-F)[28-31]. In contrast, thalidomide had no evidence for synergy when used in combination with nutlin-3 consistent with its relatively reduced effects on CK1α levels (FIG. 5B, S5E).

Figure 5C:
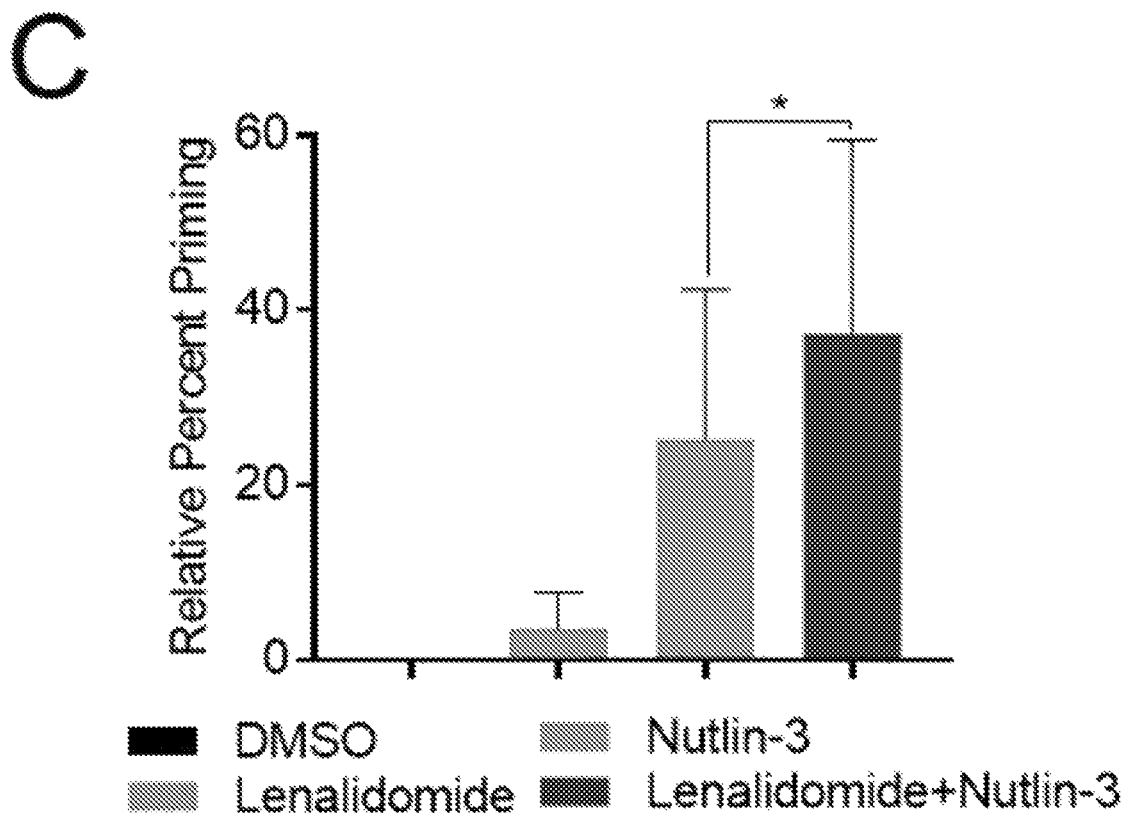
Figure 5D:
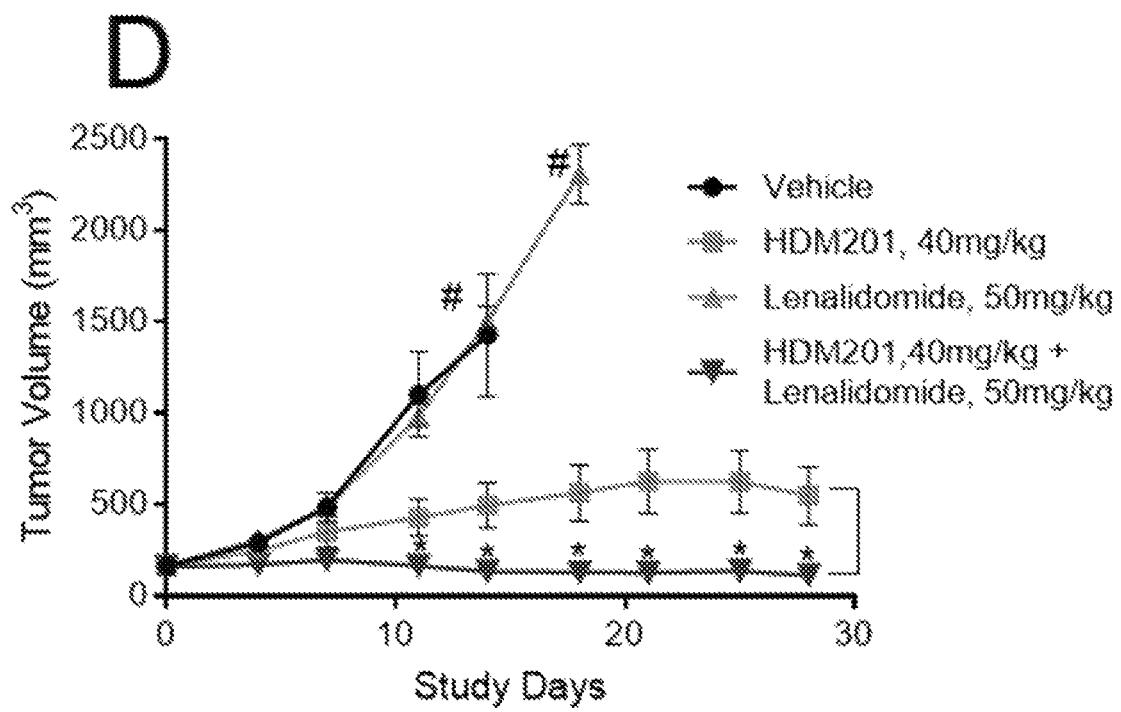
Figure 5E:
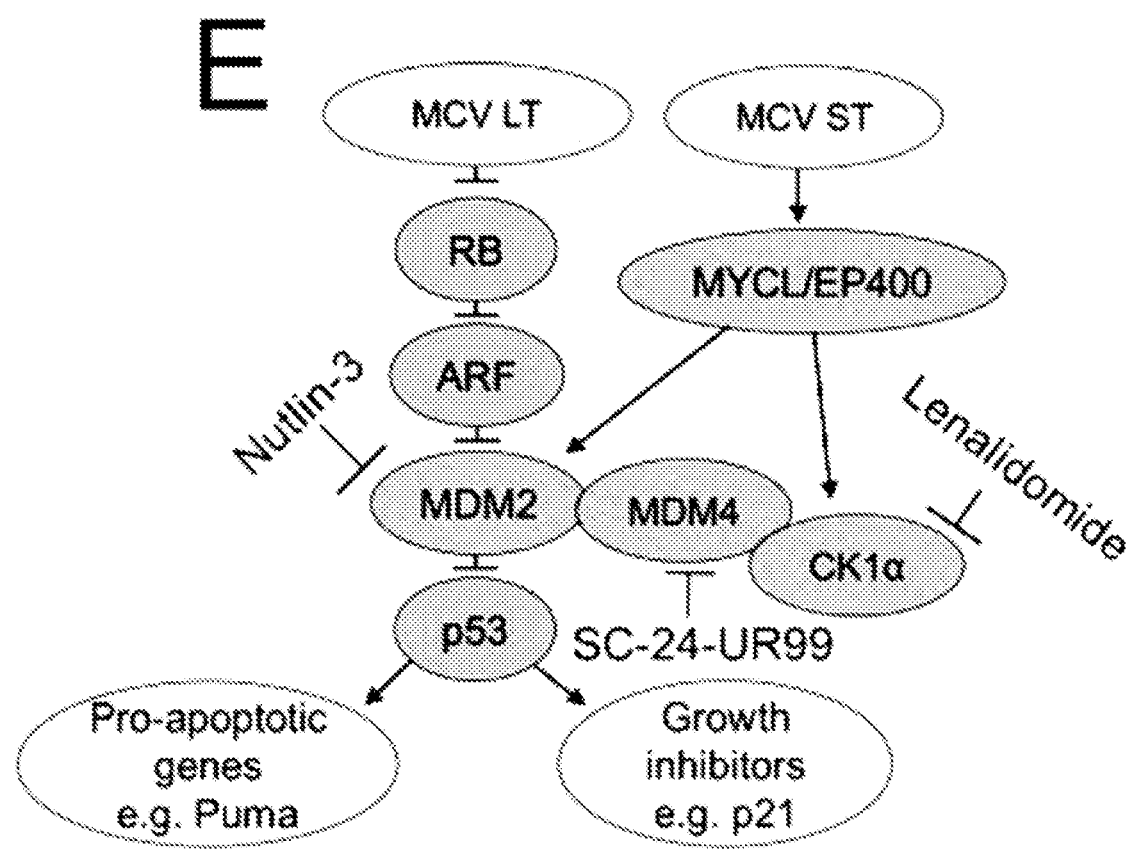

To determine if lenalidomide affected the ability of nutlin-3 to cause cell death by apoptosis in MCC cells, the present inventors performed BH3 profiling measuring sensitivity to free BH3 peptides[32]. Addition of lenalidomide to nutlin-3 enhanced the priming effect for apoptosis (FIG. 5C). To determine dual inhibition of MDM2 and MDM4 in vivo, the present inventors treated MKL-1 MCC xenografts with HDM201 (suitable for in vivo efficacy studies) with or without lenalidomide (FIG. 5D, Table S3). The present inventors found that addition of lenalidomide greatly enhances the efficacy of HDM201, providing a potential for clinical utility of the combinational therapy for p53 wild type tumors expressing MDM2 and MDM4. The present inventors propose a model where MCV T antigens increase the dependence on MDM2, MDM4 and CK1α to suppress p53 activity with therapeutic potential in virus-positive MCC (FIG. 5E).

Lenalidomide has been used to treat malignancies, myelodysplastic syndrome (MDS) and multiple myeloma (MM) [21]. It was reported that mutant CSNK1A1 predicts for a poor prognosis in lenalidomide-treated MDS[33]. Furthermore, MDS with mutant p53 respond less well to lenalidomide and is more likely to progress to acute myeloid leukemia compared to MDS with wild type p53, indicating that lenalidomide's effects may be partially dependent on inactivating MDM4[34]. The present inventors' work provides the rationale for the combination of lenalidomide with MDM2 inhibitors in MCC and in other solid tumors and hematologic malignancies containing wild type p53.

For human use, lenalidomide may be administered orally, e.g. in the form of a capsule, in accordance with the prescribing information of REVLIMID, e.g. for MM combination therapy: 25 mg once daily orally on Days 1-21 of repeated 28-day cycles; for MM maintenance therapy following auto-HSCT: 10 mg once daily continuously on Days 1-28 of repeated 28-day cycles; for MDS: 10 mg once daily; for MCL: 25 mg once daily orally on Days 1-21 of repeated 28-day cycles. Dosing is continued or modified based on clinical and laboratory findings in case of renal impairment the starting dose is adjusted based on the creatinine clearance value.

For human use, HDM201 may be administered orally, e.g. in the form of a capsule. In particular, the oral administration may use a high-dose intermittent regimen [e.g. Regimen A (50 mg-400 mg HDM201 administered on day 1 of a 3-week cycle or Regimen B (50 mg-150 mg HDM201 administered on days 1 and 8 of a 4-wk cycle) or regimen C (50 mg-500 mg HDM201 administered on day 1 of a 4-week cycle], or a low-dose extended regimen [e.g. Regimen D (10 mg-30 mg HDM201 once daily for the first 2 weeks of a 4-week cycle) or Regimen E (15 mg-50 mg HDM201 once daily for the first week of a 4-week cycle)].

For human use, idasanutlin, may be administered orally, e.g. in the form of a capsule, daily or twice daily on days 1-5 of each 28 days treatment cycle. The daily dose may be from 100 mg to 1000 mg.

For human use, SC-24-UR99 may be administered intravenously or orally, e.g. in the form of an solution or capsule. The administration may use a high-dose intermittent regimen [e.g. Regimen A (10 mg-1000 mg SC-24-UR99 administered on day 1 of a 3-week cycle or Regimen B (5 mg-500 mg SC-24-UR99 administered on days 1 and 8 of a 4-wk cycle) or regimen C (100 mg-1000 mg SC-24-UR99 administered on day 1 of a 4-week cycle], or a low-dose extended regimen [e.g. Regimen D (1 mg-100 mg SC-24-UR99 once daily for the first 2 weeks of a 4-week cycle) or Regimen E (1 mg-200 mg SC-24-UR99 once daily for the first week of a 4-week cycle)].

Chemical Formulas

The compounds mentioned herein may also be represented by the following chemical formulas.

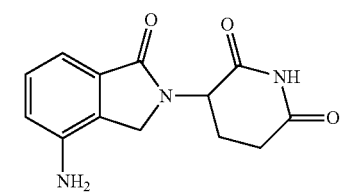

Lenalidomide

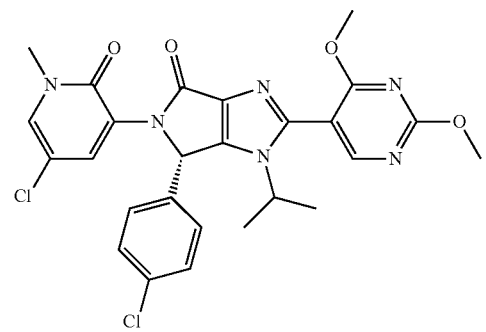

HDM201

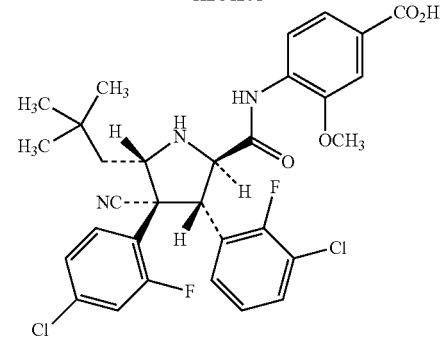

Idasanutlin

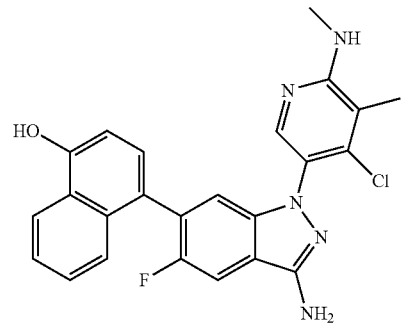

SC-24-UR99

Tables

TABLE S1

P53 targets genes significantly differentially expressed in the presence of EP400 shRNA

| Upregulated genes (>1.5) | | Downregulated genes (<−1.5) |
|---|---|---|
| VCAN | FAM183A | CBS |
| NTF3 | PKP1 | BTG2 |
| CDKN1A | CCBP2 | ASCC3 |
| LOC100294145 | PHLDA3 | TRAF4 |
| ATP2B2 | RINL | ZNF219 |
| TMEM63B | ANKRA2 | CDC42BPG |
| PLK2 | LRP1 | MDM2 |
| PTPRU | KRT18P55 | SDC1 |
| KSR1 | SERPINB5 | PGPEP1 |
| CMBL | RNF157-AS1 | TP53I3 |
| PLEKHG1 | COL17A1 | DRAM1 |
| DDIT4 | PTCHD4 | COL6A3 |
| RRM2B | SCN2A | LOC284385 |
| XPC | MYBPC3 | KCNN4 |
| INPP5D | CD82 | FAS |

TABLE S1-continued

P53 targets genes significantly differentially expressed in the presence of EP400 shRNA

| Upregulated genes (>1.5) | | Downregulated genes (<−1.5) |
|---|---|---|
| ABCB9 | KLHDC7A | ESRRB |
| FBXW7 | PTPRE | PVT1 |
| TP53I11 | CPN1 | |
| SULF2 | GJB5 | |
| LAMA3 | ORAI3 | |
| CEP85L | DOCK8 | |
| SESN2 | GDF15 | |
| DGKI | TNFRSF10B | |
| ASS1 | LOC284080 | |
| LOC100506343 | FLJ44511 | |
| COL5A1 | CFL1P1 | |
| EPS8L2 | DGKA | |
| LINC00663 | PRDM1 | |
| ITGA3 | ITGA9 | |
| ALOX5 | | |

TABLE S2

RT- and ChIP-qPCR primers

| | Forward | Reverse |
|---|---|---|
| RT-qPCR | | |
| ARF | CGCCGTGTCCAGATGTCG | TGCTCTATCCGCCAATCAGG |
| p21 | GGAGACTCTCAGGGTCGAA | GGATTAGGGCTTCCTCTTG |
| GDF15 | TAACCAGGCTGCGGGCCAAC | CAGCCGCACTTCTGGCGTGA |
| MDM2 | GTGAATCTACAGGGACGCCAT | CTGATCCAACCAATCACCTGAA |
| PUMA | TGGAGGGTCCTGTACAATCT | CACCTAATTGGGCTCCATCTC |
| FBXW7 | CCACTGGGCTTGTACCATGTT | CAGATGTAATTCGGCGTCGTT |
| GFP | AAGCTGACCCTGAAGTTCATCTGC | CTTGTAGTTGCCGTCGTCCTTGAA |
| EP400 | CCAGGAGAGGGAAAGAATTGAG | TTCATCGTCCACTTCGTCATC |
| CK1α | GCTAGCATCAATGCACATCTTG | CATGGCAGGCTGGTTCTATTA |
| MDM4 | ACATCAATTTCAGGGCTTCATTG | GTGGGCCATTCACTCTTCTT |
| MDM4-FL | CAGCAGGTGCGCAAGGTGAA | CTGTGCGAGAGCGAGAGTCTG |
| MDM4-S | CAGCAGGTGCGCAAGGTGAA | GCACTTTGCTGTAGTAGCAGTG |
| RPLP0 | GTGTTCGACAATGGCAGCAT | GACACCCTCCAGGAAGCGA |
| 18S rRNA | AACCCGTTGAACCCCATT | CCATCCAATCGGTAGTAGCG |
| Beta-actin | GGACTTCGAGCAAGAGATGG | AGCACTGTGTTGGCGTACAG |
| ChIP-qPCR | | |
| MDM2 | CCTACCCAAAGTGATGGGATTA | TCTGGTTGGAGAACGAAGATG |
| CK1α | CGAAATCCGTACGTCCTCTAAA | CAGTTTCCGATCGCCTAGTT |
| MYOG | CCAGATGAGACCTAAGAGAACATACCCAGGGATAAGAAGGATCAAGAC | |
| KRT9 | CCAGGGATAAGAAGGATCAAGAC | CTCTCTCCATTGTGTGGGATAAT |
| Intergenic | GACCAAGCCTAAACCATCTCC | AGGACCACCCCTGCTTAGG |

TABLE S3

Tumor Volume Change Values, % Ch = (T − T0)/T0, Abs Ch = T − T0, T - current value, T0 - initial value

| Group | Animal ID | Data Type | 0 | 4 | 7 | 11 | 14 | 18 |
|---|---|---|---|---|---|---|---|---|
| 1. Vehicle | 565 | % Ch | 0.00 | 63.65 | 259.33 | 625.24 | 1189.38 | |
| 1. Vehicle | 565 | Abs Ch | 0.00 | 108.88 | 443.60 | 1069.52 | 2034.53 | |
| 1. Vehicle | 566 | % Ch | 0.00 | 84.34 | 118.43 | 403.6 | 4585.21 | 1263.48 |
| 1. Vehicle | 566 | Abs Ch | 0.00 | 162.09 | 227.63 | 775.80 | 1124.77 | 2428.42 |
| 1. Vehicle | 568 | % Ch | 0.00 | 202.44 | 446.30 | 1343.42 | | |
| 1. Vehicle | 568 | Abs Ch | 0.00 | 291.00 | 641.55 | 1931.14 | | |
| 1. Vehicle | 573 | % Ch | 0.00 | 103.78 | 321.49 | 858.82 | 1551.86 | |
| 1. Vehicle | 573 | Abs Ch | 0.00 | 153.70 | 476.14 | 1271.95 | 2298.37 | |
| 1. Vehicle | 574 | % Ch | 0.00 | 4.68 | 36.95 | 89.08 | 166.66 | 245.11 |
| 1. Vehicle | 574 | Abs Ch | 0.00 | 6.53 | 51.56 | 124.30 | 232.55 | 342.02 |
| 1. Vehicle | 578 | % Ch | 0.00 | 136.55 | 276.44 | 864.34 | 1148.97 | |
| 1. Vehicle | 578 | Abs Ch | 0.00 | 244.09 | 494.14 | 1545.02 | 2053.81 | |
| 1. Vehicle | 586 | % Ch | 0.00 | 52.54 | 154.62 | 463.34 | 602.34 | 1361.60 |
| 1. Vehicle | 586 | Abs Ch | 0.00 | 83.73 | 246.41 | 738.37 | 959.89 | 2169.84 |
| 1. Vehicle | 599 | % Ch | 0.00 | −20.11 | −0.90 | 28.72 | 64.04 | 102.70 |
| 1. Vehicle | 599 | Abs Ch | 0.00 | −35.80 | −1.61 | 51.12 | 114.01 | 182.83 |
| 2. HDM201, 40 mg/kg | 560 | % Ch | 0.00 | 168.68 | 392.40 | 465.37 | 597.67 | 741.47 |
| 2. HDM201, 40 mg/kg | 560 | Abs Ch | 0.00 | 302.89 | 704.61 | 835.64 | 1073.19 | 1331.39 |
| 2. HDM201, 40 mg/kg | 564 | % Ch | 0.00 | 25.53 | 107.65 | 122.53 | 128.4 | 4165.70 |
| 2. HDM201, 40 mg/kg | 564 | Abs Ch | 0.00 | 66.12 | 278.82 | 317.36 | 332.66 | 429.17 |
| 2. HDM201, 40 mg/kg | 572 | % Ch | 0.00 | 16.64 | 56.29 | 125.88 | 191.55 | 234.58 |
| 2. HDM201, 40 mg/kg | 572 | Abs Ch | 0.00 | 32.34 | 109.40 | 244.65 | 372.29 | 455.90 |
| 2. HDM201, 40 mg/kg | 579 | % Ch | 0.00 | 93.53 | 123.49 | 248.58 | 295.64 | 350.27 |
| 2. HDM201, 40 mg/kg | 579 | Abs Ch | 0.00 | 133.99 | 176.91 | 356.12 | 423.53 | 501.79 |
| 2. HDM201, 40 mg/kg | 592 | % Ch | 0.00 | 6.55 | 37.00 | 101.24 | 94.41 | 114.06 |
| 2. HDM201, 40 mg/kg | 592 | Abs Ch | 0.00 | 10.51 | 59.41 | 162.53 | 151.58 | 183.12 |
| 2. HDM201, 40 mg/kg | 596 | % Ch | 0.00 | 29.08 | 27.47 | 14.09 | 41.69 | 20.72 |
| 2. HDM201, 40 mg/kg | 596 | Abs Ch | 0.00 | 44.16 | 41.71 | 21.39 | 63.30 | 31.46 |
| 2. HDM201, 40 mg/kg | 601 | % Ch | 0.00 | 14.67 | 30.43 | 37.76 | 77.45 | 81.45 |
| 2. HDM201, 40 mg/kg | 601 | Abs Ch | 0.00 | 21.14 | 43.86 | 54.43 | 111.64 | 117.41 |
| 2. HDM201, 40 mg/kg | 606 | % Ch | 0.00 | 11.44 | 28.15 | 61.17 | 56.59 | 83.83 |
| 2. HDM201, 40 mg/kg | 606 | Abs Ch | 0.00 | 14.26 | 35.09 | 76.25 | 70.55 | 104.49 |
| 3. Lenalidomide, 50 mg/kg | 570 | % Ch | 0.00 | 74.88 | 172.14 | 532.35 | 811.07 | 1406.04 |
| 3. Lenalidomide, 50 mg/kg | 570 | Abs Ch | 0.00 | 144.53 | 332.29 | 1027.58 | 1565.59 | 2714.05 |
| 3. Lenalidomide, 50 mg/kg | 571 | % Ch | 0.00 | 101.33 | 170.30 | 513.08 | 861.89 | 1123.01 |
| 3. Lenalidomide, 50 mg/kg | 571 | Abs Ch | 0.00 | 151.67 | 254.90 | 768.00 | 1290.11 | 1680.96 |
| 3. Lenalidomide, 50 mg/kg | 575 | % Ch | 0.00 | 102.10 | 232.85 | 584.49 | 936.62 | 1595.67 |
| 3. Lenalidomide, 50 mg/kg | 575 | Abs Ch | 0.00 | 182.72 | 416.69 | 1045.97 | 1676.13 | 2855.54 |
| 3. Lenalidomide, 50 mg/kg | 582 | % Ch | 0.00 | 99.96 | 199.00 | 475.00 | 702.42 | 1146.29 |
| 3. Lenalidomide, 50 mg/kg | 582 | Abs Ch | 0.00 | 171.42 | 341.29 | 814.62 | 1204.65 | 1965.88 |
| 3. Lenalidomide, 50 mg/kg | 585 | % Ch | 0.00 | 150.37 | 277.21 | 680.10 | 1182.50 | 1544.08 |
| 3. Lenalidomide, 50 mg/kg | 585 | Abs Ch | 0.00 | 196.53 | 362.30 | 888.86 | 1545.48 | 2018.05 |
| 3. Lenalidomide, 50 mg/kg | 590 | % Ch | 0.00 | 52.58 | 108.30 | 321.83 | 538.29 | 774.41 |
| 3. Lenalidomide, 50 mg/kg | 590 | Abs Ch | 0.00 | 107.98 | 222.38 | 660.89 | 1105.37 | 1590.25 |
| 3. Lenalidomide, 50 mg/kg | 594 | % Ch | 0.00 | 63.66 | 219.88 | 431.10 | 804.69 | 1719.65 |
| 3. Lenalidomide, 50 mg/kg | 594 | Abs Ch | 0.00 | 82.85 | 286.16 | 561.06 | 1047.26 | 2238.02 |
| 3. Lenalidomide, 50 mg/kg | 597 | % Ch | 0.00 | 71.12 | 209.85 | 501.46 | 779.36 | 1318.82 |
| 3. Lenalidomide, 50 mg/kg | 597 | Abs Ch | 0.00 | 113.80 | 335.77 | 802.36 | 1246.99 | 2110.15 |
| 4. HDM201, 40 mg/kg + Lenalidomide, 50 mg/kg | 561 | % Ch | 0.00 | −1.40 | −2.10 | 16.42 | −23.07 | −34.74 |
| 4. HDM201, 40 mg/kg + Lenalidomide, 50 mg/kg | 561 | Abs Ch | 0.00 | −2.27 | −3.39 | 26.56 | −37.32 | −56.20 |
| 4. HDM201, 40 mg/kg + Lenalidomide, 50 mg/kg | 569 | % Ch | 0.00 | 17.27 | 19.44 | −5.80 | −25.97 | −30.26 |
| 4. HDM201, 40 mg/kg + Lenalidomide, 50 mg/kg | 569 | Abs Ch | 0.00 | 29.95 | 33.70 | −10.05 | −45.03 | −52.47 |
| 4. HDM201, 40 mg/kg + Lenalidomide, 50 mg/kg | 576 | % Ch | 0.00 | −5.93 | 26.33 | 24.23 | 12.30 | 7.05 |
| 4. HDM201, 40 mg/kg + Lenalidomide, 50 mg/kg | 576 | Abs Ch | 0.00 | −11.37 | 50.48 | 46.45 | 23.57 | 13.51 |
| 4. HDM201, 40 mg/kg + Lenalidomide, 50 mg/kg | 583 | % Ch | 0.00 | 61.55 | 65.21 | 24.27 | −3.61 | 11.30 |
| 4. HDM201, 40 mg/kg + Lenalidomide, 50 mg/kg | 583 | Abs Ch | 0.00 | 88.79 | 94.07 | 35.02 | −5.21 | 16.29 |
| 4. HDM201, 40 mg/kg + Lenalidomide, 50 mg/kg | 584 | % Ch | 0.00 | 24.49 | 73.62 | 21.10 | −0.92 | −10.29 |
| 4. HDM201, 40 mg/kg + Lenalidomide, 50 mg/kg | 584 | Abs Ch | 0.00 | 39.84 | 119.75 | 34.33 | −1.49 | −16.74 |
| 4. HDM201, 40 mg/kg + Lenalidomide, 50 mg/kg | 591 | % Ch | 0.00 | 9.67 | 24.76 | 9.39 | −4.48 | −11.52 |
| 4. HDM201, 40 mg/kg + Lenalidomide, 50 mg/kg | 591 | Abs Ch | 0.00 | 13.86 | 35.49 | 13.46 | −6.43 | −16.51 |
| 4. HDM201, 40 mg/kg + Lenalidomide, 50 mg/kg | 595 | % Ch | 0.00 | −23.66 | −33.05 | −43.45 | −50.80 | −41.21 |

TABLE S3-continued

Tumor Volume Change Values, % Ch = (T − T0)/T0, Abs Ch = T − T0, T - current value, T0 - initial value

| Group | Animal ID | Data Type | 0 | 4 | 7 | 11 | 14 | 18 |
|---|---|---|---|---|---|---|---|---|
| 4. HDM201, 40 mg/kg + Lenalidomide, 50 mg/kg | 595 | Abs Ch | 0.00 | −30.46 | −42.56 | −55.95 | −65.41 | −53.06 |
| 4. HDM201, 40 mg/kg + Lenalidomide, 50 mg/kg | 605 | % Ch | 0.00 | −25.11 | −9.31 | −36.95 | −45.63 | −46.64 |
| 4. HDM201, 40 mg/kg + Lenalidomide, 50 mg/kg | 605 | Abs Ch | 0.00 | −48.16 | −17.86 | −70.88 | −87.52 | −89.46 |

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

By "combination" or "in combination with," it is not intended to imply that the therapy or the therapeutic agents must be administered at the same time and/or formulated for delivery together, although these methods of delivery are within the scope described herein. The therapeutic agents in the combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. It will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In embodiments, the additional therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the first therapeutic agent. In certain embodiments, the concentration of the first therapeutic agent that is required to achieve inhibition is lower when the first therapeutic agent is administered in combination with the second therapeutic agent than when the first therapeutic agent is administered individually. In certain embodiments, in a combination therapy, the concentration of the second therapeutic agent that is required to achieve inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the first therapeutic agent that is required to achieve inhibition is lower than the therapeutic dose of the first therapeutic agent as a monotherapy, e.g., 10-20%, 20-30%, 30-40%, 40-50%, 50-60%, 60-70%, 70-80%, or 80-90% lower.

The term "inhibition," "inhibitor," or "antagonist" includes a reduction in a certain parameter, e.g., an activity, of a given molecule, e.g., an immune checkpoint inhibitor. For example, inhibition of an activity, e.g., an activity of a given molecule, e.g., an inhibitory molecule, of at least 5%, 10%, 20%, 30%, 40% or more is included by this term. Thus, inhibition need not be 100%.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place.

The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors. The term "cancer" as used herein includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

As used herein, the terms "treat," "treatment" and "treating" refer to the reduction or amelioration of the progression, severity and/or duration of a disorder, e.g., a proliferative disorder, or the amelioration of one or more symptoms (preferably, one or more discernible symptoms) of the disorder resulting from the administration of one or more therapies. In specific embodiments, the terms "treat," "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "subject" refers herein to a human. The human may be an adult, an adolescent, a child, or an enfant.

The term MDM4 inhibitor herein refers to an inhibitor that preferentially binds MDM-4, disrupting p53-MDM4 binding, thus releasing sequestered p53 protein.

REFERENCES

1. Becker J C C et al. (2017) Merkel cell carcinoma. Nat Rev Dis Primers 3:17077.
2. Paulson K G et al. (2017) Merkel cell carcinoma: Current US incidence and projected increases based on changing demographics. J. Am. Acad. Dermatol.
3. Feng H, Shuda M, Chang Y, Moore P S (2008) Clonal integration of a polyomavirus in human merkel cell carcinoma. Science (New York, N.Y.) 319(5866):1096-1100.10.1126/science. 1152586.
4. Rodig S J et al. (2012) Improved detection suggests all Merkel cell carcinomas harbor Merkel polyomavirus. The Journal of clinical investigation 122(12):4645-4653.10.1172/JCI64116.
5. Shuda M, Kwun H J, Feng H, Chang Y, Moore P S (2011) Human Merkel cell polyomavirus small t antigen is an oncoprotein targeting the 4e-bp1 translation regulator. The Journal of clinical investigation 121(9):3623-3634. 10.11723C146323.
6. Cheng J, Rozenblatt-Rosen O, Paulson K G, Nghiem P, DeCaprio J A (2013) Merkel cell polyomavirus large t antigen has growth-promoting and inhibitory activities. Journal of virology 87(11):6118-6126. 10.1128/W1.00385-13.
7. Starrett G J et al. (2017) Merkel cell polyomavirus exhibits dominant control of the tumor genome and transcriptome in virus-associated Merkel cell carcinoma. mBio 8(1). 10.1128/mBio.02079-16.
8. Harms P W et al. (2015) The distinctive mutational spectra of polyomavirus-negative Merkel cell carcinoma. Cancer research 75(18):3720-3727. 10.1158/0008-5472.CAN-15-0702.
9. Allen M A et al. (2014) Global analysis of p53-regulated transcription identifies its direct targets and unexpected regulatory mechanisms. eLife 3. 10.7554/elife.02200.
10. Bates S et al. (1998) p14ARF links the tumour suppressors RB and p53. Nature 395(6698):124-5.
11. Nomura K et al. (2017) Structural analysis of MDM2 RING separates degradation from regulation of p53 transcription activity. Nat. Struct. Mol. Biol. 24(7):578-587.
12. Bista M, Petrovich M, Fersht A R (2013) MDMX contains an autoinhibitory sequence element. Proc. Natl. Acad. Sci. U.S.A. 110(44):17814-9.
13. Chen L et al. (2015) Autoinhibition of MDMX by intramolecular p53 mimicry. Proc. Natl. Acad. Sci. U.S.A. 112(15):4624-9.
14. Beliveau A, Yaswen P (2007) Soothing the watchman: telomerase reduces the p53-dependent cellular stress response. Cell cycle (Georgetown, Tex.) 6(11):1284-1287. 10.4161/cc.6.11.4298.
15. Cheng J et al. (2017) Merkel cell polyomavirus recruits myc1 to the ep400 complex to promote oncogenesis. PLOS Pathogens 13(10):1-31.
16. Arora R et al. (2012) Survivin is a therapeutic target in merkel cell carcinoma. Sci Transl Med 4(133):133ra56.
17. Berrios C et al. (2016) Merkel cell polyomavirus small t antigen promotes pro-glycolytic metabolic perturbations required for transformation. PLoS pathogens 12(11). 10.1371/journal. ppat.1006020.
18. Lenos K et al. (2012) Alternate splicing of the p53 inhibitor hdmx offers a superior prognostic biomarker than p53 mutation in human cancer. Cancer Research 72(16):4074-4084. 10.1158/0008-5472.CAN-12-0215.
19. Sholl L M et al. (2016) Institutional implementation of clinical tumor profiling on an unselected cancer population. JCI Insight 1(19):e87062.
20. Bonbon R et al. (2013) Mechanisms of p53 restriction in merkel cell carcinoma cells are independent of the merkel cell polyoma virus t antigens. The Journal of investigative dermatology 133(10):2453-2460.10.1038/jid.2013.169.
21. Krönke J et al. (2015) Lenalidomide induces ubiquitination and degradation of ck1alpha in del(5q) mds. Nature 523(7559):183-188. 10.1038/nature14610.
22. Petzold G, Fischer E S, Thomä NH (2016) Structural basis of lenalidomide-induced CK1α degradation by the CRL4(CRBN) ubiquitin ligase. Nature 532(7597):127-30.
23. Spiotto M T et al. (2010) Imaging the unfolded protein response in primary tumors reveals microenvironments with metabolic variations that predict tumor growth. Cancer Res. 70(1):78-88.
24. Doench J G et al. (2016) Optimized sgRNA design to maximize activity and minimize off-target effects of CRISPR-Cas9. Nat. Biotechnol. 34(2):184-191.
25. Zhou B et al. (2001) HER-2/neu induces p53 ubiquitination via akt-mediated MDM2 phosphorylation. Nat. Cell Biol. 3(11):973-82.
26. Furet P et al. (2016) Discovery of a novel class of highly potent inhibitors of the p53-MDM2 interaction by structure-based design starting from a conformational argument. Bioorg. Med. Chem. Lett. 26(19):4837-4841.
27. Scudiero D et al. (1988) Evaluation of a soluble tetrazolium/formazan assay for cell growth and drug sensitivity in culture using human and other tumor cell lines. Cancer Res. 48(17):4827-33.
28. Chou T, Motzer R, Tong Y, Bosl G (1994) Computerized quantitation of synergism and antagonism of taxol, topotecan, and cisplatin against human teratocarcinoma cell growth: a rational approach to clinical protocol design. J. Natl. Cancer Inst. 86(20):1517-24.
29. Ianevski A, He L, Aittokallio T, Tang J (2017) SynergyFinder: a web application for analyzing drug combination dose-response matrix data. Bioinformatics 33(15):2413-2415.

30. Ding Q et al. (2013) Discovery of rg7388, a potent and selective p53-mdm2 inhibitor in clinical development. Journal of medicinal chemistry 56(14):5979-5983.10.1021/jm400487c.
31. Sun D et al. (2014) Discovery of amg 232, a potent, selective, and orally bioavailable mdm2-p53 inhibitor in clinical development. Journal of medicinal chemistry 57(4):1454-1472. 10.1021/jm401753e.
32. Montero J et al. (2015) Drug-induced death signaling strategy rapidly predicts cancer response to chemotherapy. Cell 160(5):977-89.
33. Smith A E et al. (2015) CSNK1A1 mutations and isolated del(5q) abnormality in myelodysplastic syndrome: a retrospective mutational analysis. Lancet Haematol 2(5):e212-21.
34. Saft L et al. (2014) p53 protein expression independently predicts outcome in patients with lower-risk myelodysplastic syndromes with del(5q). Haematologica 99(6):1041-9.
35. Cronin J, Zhang X Y Y, Reiser J (2005) Altering the tropism of lentiviral vectors through pseudotyping. Current gene therapy 5(4):387-398. 10.2174/1566523054546224.
36. Pallis M et al. (2016) Complementary dynamic bh3 profiles predict co-operativity between the multi-kinase inhibitor tg02 and the bh3 mimetic abt-199 in acute myeloid leukaemia cells. Oncotarget. 10.18632/oncotarget.8742.
37. Schmidt D et al. (2009) Chip-seq: Using high-throughput sequencing to discover protein-dna interactions. Methods 48(3):240-248. 10.1016/j.ymeth.2009.03.001.

EXAMPLES

Materials and Methods.
Plasmids

The GFP and T antigen cDNAs were Gateway (Invitrogen) cloned into pLIX-402 inducible empty or pLenti CMV Blast empty vector (w263-1), obtained from David Root (Addgene plasmid 141394) and Eric Campeau (Addgene plasmid 17486), respectively. The sgRNA clones for CK1α (BRDN0001149315, BRDN0001145680) were obtained from John Doench and David Root (Addgene plasmid 76188, 76189). pLKO-p53-shRNA-941 was obtained from Todd Waldman (Addgene plasmid 25637).
Cell and Cell Culture To generate cell lines stably expressing these constructs, IMR90 human lung fibroblast, HCT116 colon carcinoma or MKL-1 MCC cells were transduced using a three vector lentivirus transduction system (15). MCC cell lines were obtained from Masa Shuda (University of Pittsburgh, Pa.), Jürgen Becker (Medical University Graz, Austria), and Roland Houben (University of Wuerzburg, Germany). 293T, HCT116 and IMR90 cells were obtained from ATCC. Generation of MKL-1 MCC cell lines inducibly expressing shRNAs and IMR90 transformation using p53DD, MYCL and hTERT constructs was described previously (17). IMR90 and human primary foreskin fibroblast cells (HFF) were cultured in DMEM supplemented with 15% FBS, antibiotics and non-essential amino acids and MCC cell lines were grown in RPMI supplemented with 10% FBS and antibiotics.
Cell Viability Assay Nutlin-3 (Cayman chemical), Lenalidomide (Cayman chemical), Thalidomide (Santa Cruz Biotechnology), Pomalidomide (Selleck chemicals), AMG232 (MedChem Express), RG7388 (from Aileron Therapeutics), HDM201 (Novartis Pharmaceuticals), SC-24-UR99 (Novartis Pharmaceuticals), Cycloheximide (Sigma-Aldrich), and MG132 (Boston Biochem) were reconstituted in DMSO and added directly to culture media. Cell viability assays were performed using Cell Proliferation Kit II (XTT) (Roche) according to the manufacturer's instructions and BH3 profiling was described in Pallis et al. (36). Synergy testing was performed using Compusyn and Synergyfinder (28, 29).
Immunoprecipitation, Immunoblotting, and Antibodies.

Confluent cultures of cells were washed with ice-cold phosphate-buffered saline (PBS) and resuspended in EBC lysis buffer (50 mM Tris, pH 8.0, 150 mM NaCl, 0.5% NP-40, 1:10,000-mercaptoethanol, 0.5 mM EDTA) for 10 min on ice and then centrifuged. Clarified lysates were incubated overnight with antibodies and magnetic protein A/G beads (PureProteome magnetic beads, EMD Millipore). The beads were washed with high-salt EBC buffer (50 mM Tris, pH 8.0, 300 mM NaCl, 0.5% NP-40, 0.5 mM EDTA) 5 times and boiled in Laemmli sample buffer prior to SDS polyacrylamide gel electrophoresis Immunoprecipitation and western blotting were performed with antibodies to MDM4 (17914-1-AP; Proteintech Group), MDM2 (SMP14, Santa Cruz biotechnology), CK1α (17125-1-AP; Proteintech Group), phospho-Ser166 MDM2 (]3521, Cell Signaling Technology), Phopho-Ser15 p53 (]9284; Cell Signaling Technology), acetyl-Lys382 p53 (12525; Cell Signaling Technology), p21 (]2946; Cell Signaling Technology), PUMA (]12450; Cell Signaling Technology), VPS39 (ab107570; Abcam), PARP (19542; Cell Signaling Technology), GFP (12555; Cell Signaling Technology), MYCL (14584-1-AP; Proteintech Group), p53 (D0-1; Thermo Scientific/Lab Vision), and RB1 (G3-245; BD Biosciences). Mouse monoclonal antibodies Ab3 and Ab5 against MCV T antigens were generated against MCV large T antigen residues 1 to 260 and produced as a glutathione S-transferase (GST) fusion protein in bacteria (17). Quantitative western blotting was performed using the Odyssey near-infrared system (Li-Cor Biotechnology).
ChIP- and RT-qPCR The ChIP method was modified from protocols described in Schmidt et al. (37). MKL-1 cells or IMR90 cells were cross-linked using dual cross-linking with disuccinimidyl glutarate (DSG) and formaldehyde. After cross-linking, cells were lysed using SimpleChIP buffer A and B (Cell signaling) and DNA was processed with micrococcal nuclease (New England Biolabs Inc.) for 30 minutes at 37° C. followed by sonicating for 20 second pulses 5 times at 4° C. For RT-qPCR, total RNA was purified using RNeasy Plus Mini Kit (Qiagen) and cDNA was synthesized using High-Capacity cDNA reverse transcription kit (Applied Biosystems). Quantitative PCR was performed using Brilliant III Ultra-Fast SYBR Green qPCR Master Mix (Agilent Technologies). The primer information can be found in Supplementary table 2.
Xenograft Efficacy Study NSG mice of 7 to 9 weeks old age (the Jackson laboratory) were injected with 1.00e+007 MKL-1 MCC cells. When the tumor reached the size of 200 mm3, a group of 8 mice were treated daily with vehicle, HDM201 (from Novartis Pharmaceuticals, 40 mg/kg, 0.5% methylcellulose (400 cP) in 50 mM phosphate buffer, pH 6.8, oral), lenalidomide (MedChemExpress, 50 mg/kg, 0.5% CMC+0.25% Tween 80, oral) or both HDM201 and lenalidomide. The study was terminated when the tumor volume reached the maximum permissible size of 2000 mm3.

Some of the experiments performed and the results obtained are disclosed herein in the detailed description of the invention section and in the figures and their description.

Example 1

The following tables provide the data from synergy testing of various combinations of drugs/compounds in reducing viability of MKL-1 MCC cells. MKL-1 (virus-positive Merkel cell carcinoma cell line with wild type p53) were treated for 96 hours. The XTT assay was performed to determine the relative viability (% response) normalized to untreated cells. Separate tables include data for combinations 1. Nutlin-Lenalidomide 2. Nutlin-UR99 3. HDM201-UR99 4. Nutlin-3+/−lenalidomide; RG7388+/−Lenalidomide; Lenalidomide alone 5. HDM201+Lenalidomide.

| Drug1 | Drug2 | Conc1 | Conc2 | Response | ConcUnit |
|---|---|---|---|---|---|
| Lenalidomide | Nutlin-3 | 0 | 0 | 100 | nM |
| Lenalidomide | Nutlin-3 | 5000 | 0 | 104.85 | nM |
| Lenalidomide | Nutlin-3 | 10000 | 0 | 105.06 | nM |
| Lenalidomide | Nutlin-3 | 15000 | 0 | 107.06 | nM |
| Lenalidomide | Nutlin-3 | 18000 | 0 | 100.64 | nM |
| Lenalidomide | Nutlin-3 | 0 | 1250 | 82.16 | nM |
| Lenalidomide | Nutlin-3 | 5000 | 1250 | 51.05 | nM |
| Lenalidomide | Nutlin-3 | 10000 | 1250 | 48.71 | nM |
| Lenalidomide | Nutlin-3 | 15000 | 1250 | 52.74 | nM |
| Lenalidomide | Nutlin-3 | 18000 | 1250 | 46 | nM |
| Lenalidomide | Nutlin-3 | 0 | 2500 | 65.56 | nM |
| Lenalidomide | Nutlin-3 | 5000 | 2500 | 35.92 | nM |
| Lenalidomide | Nutlin-3 | 10000 | 2500 | 35.85 | nM |
| Lenalidomide | Nutlin-3 | 15000 | 2500 | 36.1 | nM |
| Lenalidomide | Nutlin-3 | 18000 | 2500 | 33.84 | nM |
| Lenalidomide | Nutlin-3 | 0 | 3750 | 44.2 | nM |
| Lenalidomide | Nutlin-3 | 5000 | 3750 | 25.46 | nM |
| Lenalidomide | Nutlin-3 | 10000 | 3750 | 26.75 | nM |
| Lenalidomide | Nutlin-3 | 15000 | 3750 | 28.79 | nM |
| Lenalidomide | Nutlin-3 | 18000 | 3750 | 27.94 | nM |
| Lenalidomide | Nutlin-3 | 0 | 4500 | 41.19 | nM |
| Lenalidomide | Nutlin-3 | 5000 | 4500 | 23.51 | nM |
| Lenalidomide | Nutlin-3 | 10000 | 4500 | 26.37 | nM |
| Lenalidomide | Nutlin-3 | 15000 | 4500 | 22.99 | nM |
| Lenalidomide | Nutlin-3 | 18000 | 4500 | 24.53 | nM |
| SC-24-UR99 | Nutlin-3 | 0 | 0 | 100 | nM |
| SC-24-UR99 | Nutlin-3 | 50 | 0 | 103.6933 | nM |
| SC-24-UR99 | Nutlin-3 | 100 | 0 | 99.5168 | nM |
| SC-24-UR99 | Nutlin-3 | 150 | 0 | 99.3633 | nM |
| SC-24-UR99 | Nutlin-3 | 180 | 0 | 92.5016 | nM |
| SC-24-UR99 | Nutlin-3 | 0 | 1250 | 96.8309 | nM |
| SC-24-UR99 | Nutlin-3 | 50 | 1250 | 51.4828 | nM |
| SC-24-UR99 | Nutlin-3 | 100 | 1250 | 44.9011 | nM |
| SC-24-UR99 | Nutlin-3 | 150 | 1250 | 35.9542 | nM |
| SC-24-UR99 | Nutlin-3 | 180 | 1250 | 38.5128 | nM |
| SC-24-UR99 | Nutlin-3 | 0 | 2500 | 72.5696 | nM |
| SC-24-UR99 | Nutlin-3 | 50 | 2500 | 26.7148 | nM |
| SC-24-UR99 | Nutlin-3 | 100 | 2500 | 22.6589 | nM |
| SC-24-UR99 | Nutlin-3 | 150 | 2500 | 22.0257 | nM |
| SC-24-UR99 | Nutlin-3 | 180 | 2500 | 21.9253 | nM |
| SC-24-UR99 | Nutlin-3 | 0 | 3750 | 63.6648 | nM |
| SC-24-UR99 | Nutlin-3 | 50 | 3750 | 22.7101 | nM |
| SC-24-UR99 | Nutlin-3 | 100 | 3750 | 22.892 | nM |
| SC-24-UR99 | Nutlin-3 | 150 | 3750 | 21.6436 | nM |
| SC-24-UR99 | Nutlin-3 | 180 | 3750 | 21.8598 | nM |
| SC-24-UR99 | Nutlin-3 | 0 | 4500 | 56.8421 | nM |
| SC-24-UR99 | Nutlin-3 | 50 | 4500 | 23.6636 | nM |
| SC-24-UR99 | Nutlin-3 | 100 | 4500 | 22.4951 | nM |
| SC-24-UR99 | Nutlin-3 | 150 | 4500 | 23.0683 | nM |
| SC-24-UR99 | Nutlin-3 | 180 | 4500 | 21.8378 | nM |
| SC-24-UR99 | HDM201 | 0 | 0 | 100 | nM |
| SC-24-UR99 | HDM201 | 50 | 0 | 100.5561 | nM |
| SC-24-UR99 | HDM201 | 100 | 0 | 105.263 | nM |
| SC-24-UR99 | HDM201 | 150 | 0 | 93.4308 | nM |
| SC-24-UR99 | HDM201 | 180 | 0 | 89.8385 | nM |
| SC-24-UR99 | HDM201 | 0 | 50 | 93.9107 | nM |
| SC-24-UR99 | HDM201 | 50 | 50 | 72.9123 | nM |
| SC-24-UR99 | HDM201 | 100 | 50 | 59.4628 | nM |
| SC-24-UR99 | HDM201 | 150 | 50 | 45.9284 | nM |
| SC-24-UR99 | HDM201 | 180 | 50 | 42.8791 | nM |
| SC-24-UR99 | HDM201 | 0 | 100 | 90.5417 | nM |
| SC-24-UR99 | HDM201 | 50 | 100 | 54.0118 | nM |
| SC-24-UR99 | HDM201 | 100 | 100 | 49.0179 | nM |
| SC-24-UR99 | HDM201 | 150 | 100 | 40.2345 | nM |
| SC-24-UR99 | HDM201 | 180 | 100 | 35.2668 | nM |
| SC-24-UR99 | HDM201 | 0 | 150 | 94.8184 | nM |
| SC-24-UR99 | HDM201 | 50 | 150 | 61.1783 | nM |
| SC-24-UR99 | HDM201 | 100 | 150 | 46.8796 | nM |
| SC-24-UR99 | HDM201 | 150 | 150 | 35.6452 | nM |
| SC-24-UR99 | HDM201 | 180 | 150 | 31.2955 | nM |
| SC-24-UR99 | HDM201 | 0 | 180 | 87.8557 | nM |
| SC-24-UR99 | HDM201 | 50 | 180 | 50.8719 | nM |
| SC-24-UR99 | HDM201 | 100 | 180 | 40.5355 | nM |
| SC-24-UR99 | HDM201 | 150 | 180 | 32.0859 | nM |
| SC-24-UR99 | HDM201 | 180 | 180 | 29.2436 | nM |

| Drug1 | Drug2 | Conc1 | Conc2 | Response-rep1 | Response-rep2 | rep1 raw | rep2 | rep2 ConcUnit |
|---|---|---|---|---|---|---|---|---|
| Lenalidomide | HDM201 | 0 | 0 | 100 | 100 | 1.3383 | 1.5094 | nM |
| Lenalidomide | HDM201 | 5000 | 0 | 98.9539 | 97.72758 | 1.3243 | 1.4751 | nM |
| Lenalidomide | HDM201 | 10000 | 0 | 83.3296 | 76.26209 | 1.1152 | 1.1511 | nM |
| Lenalidomide | HDM201 | 15000 | 0 | 69.78256 | 67.82165 | 0.9339 | 1.0237 | nM |
| Lenalidomide | HDM201 | 18000 | 0 | 25.1812 | 49.26461 | 0.337 | 0.7436 | nM |
| Lenalidomide | HDM201 | 0 | 50 | 90.75693 | 92.94421 | 1.2146 | 1.4029 | nM |
| Lenalidomide | HDM201 | 5000 | 50 | 77.60592 | 78.13701 | 1.0386 | 1.1794 | nM |
| Lenalidomide | HDM201 | 10000 | 50 | 67.27938 | 55.88976 | 0.9004 | 0.8436 | nM |
| Lenalidomide | HDM201 | 15000 | 50 | 31.12904 | 25.18882 | 0.4166 | 0.3802 | nM |
| Lenalidomide | HDM201 | 18000 | 50 | 13.24068 | 13.03829 | 0.1772 | 0.1968 | nM |
| Lenalidomide | HDM201 | 0 | 100 | 75.79765 | 77.71962 | 1.0144 | 1.1731 | nM |
| Lenalidomide | HDM201 | 5000 | 100 | 46.64873 | 51.47078 | 0.6243 | 0.7769 | nM |
| Lenalidomide | HDM201 | 10000 | 100 | 23.56721 | 37.25984 | 0.3154 | 0.5624 | nM |
| Lenalidomide | HDM201 | 15000 | 100 | 12.76246 | 14.34345 | 0.1708 | 0.2165 | nM |
| Lenalidomide | HDM201 | 18000 | 100 | 11.42494 | 11.56751 | 0.1529 | 0.1746 | nM |
| Lenalidomide | HDM201 | 0 | 150 | 53.3961 | 61.83914 | 0.7146 | 0.9334 | nM |
| Lenalidomide | HDM201 | 5000 | 150 | 15.87835 | 29.39579 | 0.2125 | 0.4437 | nM |
| Lenalidomide | HDM201 | 10000 | 150 | 12.42621 | 17.77527 | 0.1663 | 0.2683 | nM |
| Lenalidomide | HDM201 | 15000 | 150 | 12.80729 | 15.48297 | 0.1714 | 0.2337 | nM |
| Lenalidomide | HDM201 | 18000 | 150 | 12.25435 | 12.91904 | 0.164 | 0.195 | nM |
| Lenalidomide | HDM201 | 0 | 180 | 33.31839 | 40.87055 | 0.4459 | 0.6169 | nM |
| Lenalidomide | HDM201 | 5000 | 180 | 13.27057 | 19.14668 | 0.1776 | 0.289 | nM |

-continued

| | | | | | | | | |
|---|---|---|---|---|---|---|---|---|
| Lenalidomide | HDM201 | 10000 | 180 | 13.07629 | 14.60183 | 0.175 | 0.2204 | nM |
| Lenalidomide | HDM201 | 15000 | 180 | 14.93686 | 16.28462 | 0.1999 | 0.2458 | nM |
| Lenalidomide | HDM201 | 18000 | 180 | 13.98042 | 12.76004 | 0.1871 | 0.1926 | nM |

With a fixed amount of Lenalidomide (5 uM)

| Nutlin-3 or RG7388 | Nutlin-3 | | | Nutlin-3 + Lenalidomide | | | RG7388 |
|---|---|---|---|---|---|---|---|
| 0 | 1 | 1 | 1 | 1 | 1 | 1 | 1 |
| 25 | 0.662584 | 0.59335 | 0.649785 | 0.249101 | 0.246948 | 0.268225 | 0.78191 |
| 50 | 0.381798 | 0.397717 | 0.393338 | 0.175281 | 0.185707 | 0.182002 | 0.683595 |
| 75 | 0.266742 | 0.19196 | 0.285781 | 0.163034 | 0.167643 | 0.172669 | 0.553034 |
| 90 | 0.233258 | 0.187692 | 0.27767 | 0.155056 | 0.155732 | 0.164446 | 0.466292 |

With a fixed amount of Lenalidomide (5 uM)

| RG7388 | | RG7388 + Lenalidomide | | | Lenalidomide | | |
|---|---|---|---|---|---|---|---|
| 1 | 1 | 1 | 1 | 1 | 1 | 1 | 1 |
| 0.711067 | 0.822231 | 0.326404 | 0.349082 | 0.380782 | 1.143371 | 0.884466 | 1.021567 |
| 0.581439 | 0.688452 | 0.265393 | 0.272854 | 0.286892 | 1.089326 | 0.938362 | 1.081456 |
| 0.433846 | 0.543117 | 0.202921 | 0.202084 | 0.220225 | 1.027416 | 1.060546 | 1.086012 |
| 0.369529 | 0.510783 | 0.204045 | 0.189777 | 0.195558 | 1.011348 | 0.945012 | 0.952122 |

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A pharmaceutical composition comprising (a) a mouse double minute 2 (MDM2) inhibitor which is HDM201 ((S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one) or nutlin-3 and (b) i) a Casein Kinase 1 alpha (CK1α) degrading agent which is lenalidomide and/or ii) a mouse double minute 4 (MDM4) inhibitor which is SC-24-UR-99 (4-(3-amino-1-(4-chloro-5-methyl-6-(methylamino)pyridin-3-yl)-5-fluoro-1H-indazol-6-yl)naphthalen-1-ol).

2. The composition of claim 1, wherein (a) is HDM201.

3. The composition of claim 1, wherein (a) is nutlin-3.

4. The composition of claim 1, wherein (a) is HDM201 and (b) is lenalidomide.

5. The composition of claim 1, wherein (a) is HDM201 and (b) is SC-24-UR99.

6. The composition of claim 1, wherein (a) is HDM201 and (b) is lenalidomide and SC-24-UR99.

7. A method of treating a p53 wild type (WT) tumor in a subject, comprising administering to the subject (a) an MDM2 inhibitor which is HDM201 or nutlin-3 and (b) i) a CK1α degrading agent which is lenalidomide and/or ii) an MDM4 inhibitor which is SC-24-UR-99.

8. The method of claim 7, wherein (a) is HDM201.

9. The method of claim 7, wherein (a) is nutlin-3.

10. The method of claim 7, wherein (a) is HDM201 and (b) is lenalidomide.

11. The method of claim 7, wherein (a) is HDM201 and (b) is SC-24-UR99.

12. The method of claim 7, wherein (a) is HDM201 and (b) is lenalidomide and SC-24-UR99.

13. The method of claim 7, wherein the p53 WT tumor is a solid tumor.

14. The method of claim 13, wherein the solid tumor is selected from the group consisting of sarcomas, liposarcoma, soft tissue sarcoma, lymphomas, non-Hodgkin's lymphoma (NHL), Mantle cell lymphoma (MCL), melanomas, skin melanoma, uveal melanoma, blastomas, neuroblastoma, colon tumor, colorectal tumor, kidney tumor, liver tumor, skin cancer, and Merkel cell carcinoma (MCC).

15. The method of claim 14, wherein the solid tumor is a Merkel cell carcinoma (MCC).

16. The method of claim 14, wherein the Merkel cell carcinoma (MCC) is a Merkel cell polyomavirus (MCV)-positive MCC.

17. The method of claim 7, wherein the p53 WT tumor is a hematological tumor or a hematologic malignancy.

18. The method of claim 17, wherein the hematological tumor is selected from the group consisting of acute myeloid leukemia (AML), multiple myeloma (MM), myelodysplastic syndrome (MDS), and acute lymphoblastic leukemia (ALL).

19. The method of claim 17, wherein the hematological tumor is multiple myeloma (MM) or myelodysplastic syndrome (MDS).

20. The method of claim 19, wherein the hematological tumor is myelodysplastic syndrome (MDS).

21. The method of claim 7, wherein (a) is HDM201, wherein (b) is lenalidomide, and wherein the p53 WT tumor is MCV-positive MCC.

22. The method of claim 7, wherein (a) is HDM201, wherein (b) is lenalidomide, and wherein the p53 WT tumor is MDS.

23. The method of claim 7, further comprising one or more further anti-cancer agent(s).

* * * * *